United States Patent
Heck et al.

(10) Patent No.: US 10,941,125 B2
(45) Date of Patent: *Mar. 9, 2021

(54) PROXISOME PROLIFERATOR ACTIVATED RECEPTOR (PPAR) COMPOUNDS AND METHODS OF USING THE SAME

(71) Applicant: The University of Toledo, Toledo, OH (US)

(72) Inventors: Bruce E. Heck, Toledo, OH (US); Dong Hyun Kim, Toledo, OH (US); Paul W. Erhardt, Toledo, OH (US); Brian Kress, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,815

(22) Filed: Jul. 8, 2019

(65) Prior Publication Data
US 2019/0330166 A1    Oct. 31, 2019

Related U.S. Application Data

(62) Division of application No. 15/593,750, filed on May 12, 2017, now Pat. No. 10,351,541, which is a division of application No. 14/773,022, filed as application No. PCT/US2014/027817 on Mar. 14, 2014, now Pat. No. 9,695,137.

(60) Provisional application No. 61/786,030, filed on Mar. 14, 2013.

(51) Int. Cl.
| | | |
|---|---|---|
| C07D 277/26 | (2006.01) | |
| C07D 277/28 | (2006.01) | |
| A61K 31/426 | (2006.01) | |
| C07D 277/24 | (2006.01) | |
| A61K 31/5575 | (2006.01) | |
| A61K 45/06 | (2006.01) | |
| C07D 277/22 | (2006.01) | |

(52) U.S. Cl.
CPC .......... *C07D 277/24* (2013.01); *A61K 31/426* (2013.01); *A61K 31/5575* (2013.01); *A61K 45/06* (2013.01); *C07D 277/22* (2013.01); *C07D 277/28* (2013.01)

(58) Field of Classification Search
CPC ... C07D 277/26; C07D 277/28; A61K 31/426
See application file for complete search history.

(56) References Cited

U.S. PATENT DOCUMENTS

2003/0203947 A1* 10/2003 Chao .................. A61P 3/00
514/365

OTHER PUBLICATIONS

Bhatt et al. Chem. Biol. Drug Des., 2011, vol. 77, pp. 361-372.*

* cited by examiner

*Primary Examiner* — Samira J Jean-Louis
(74) *Attorney, Agent, or Firm* — MacMillan, Sobanski & Todd, LLC

(57) ABSTRACT

Peroxisome proliferator activated receptor (PPAR) compounds, and methods of using the same for treating bone fractures, treating osteoporosis and/or metabolic bone diseases, and inducing osteogenesis and/or chondrogenesis, are disclosed.

3 Claims, 23 Drawing Sheets
(11 of 23 Drawing Sheet(s) Filed in Color)

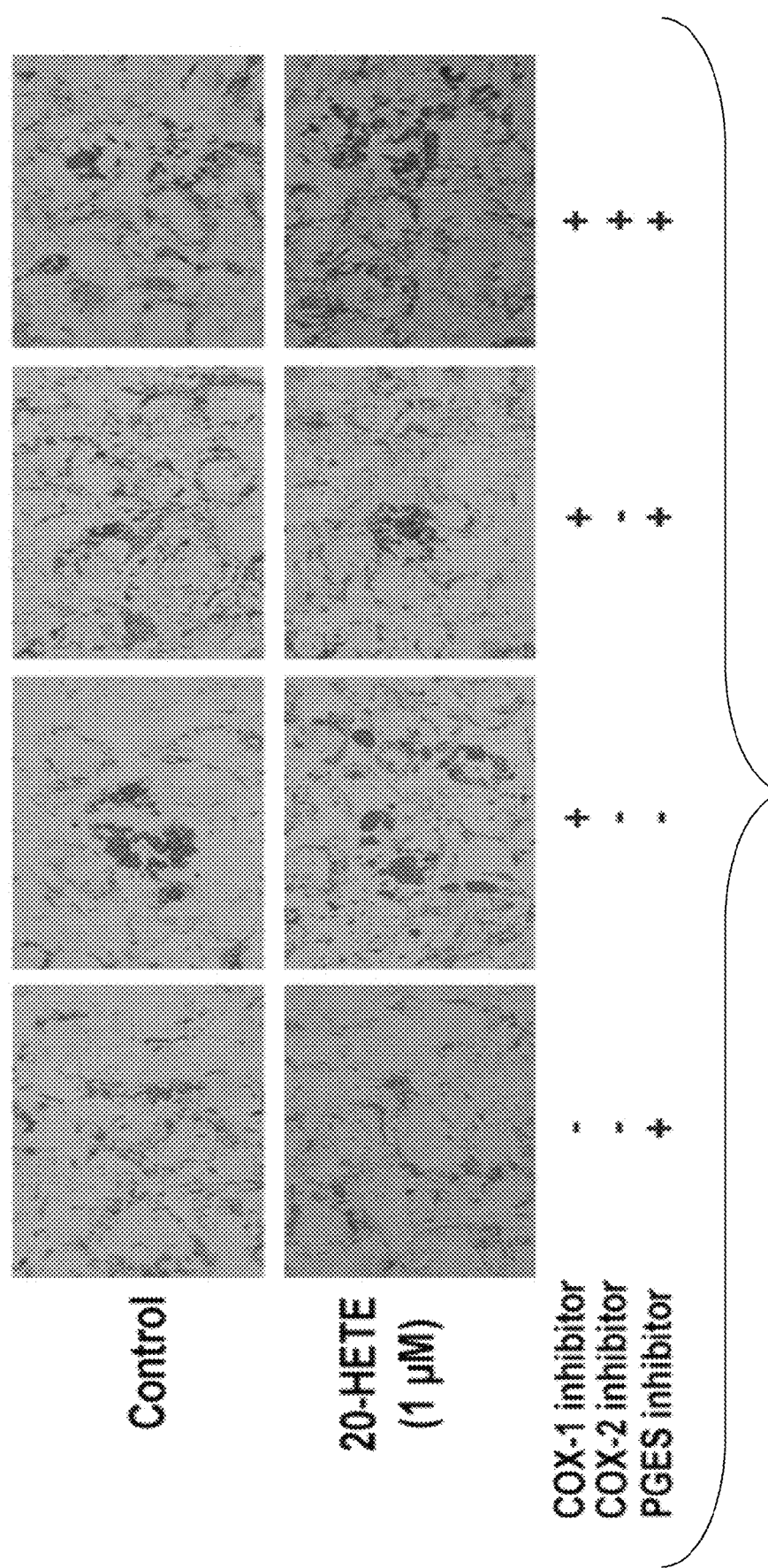

Table 1 - Differential effects on stem cells when treated with 6a – 6c.

| Cmpd | R₁ | R₂ | Adipogenesis | Osteogenesis |
|---|---|---|---|---|
| GW0742 | Standard Agent | | 0 | + + + |
| 6a | H | H | + + + | 0 |
| 6b | CF₃ | H | + + | + + |
| 6c | H | CF₃ | + | + + + |

PROXISOME PROLIFERATOR ACTIVATED RECEPTOR (PPAR) COMPOUNDS AND METHODS OF USING THE SAME

RELATED APPLICATIONS

The present application is a divisional application of U.S. Ser. No. 15/593,750 filed May 12, 2017, now U.S. Pat. No. 10,351,541 issued Jul. 16, 2019, which a divisional application of U.S. Ser. No. 14/773,022 filed Sep. 4, 2015, now U.S. Pat. No. 9,695,137 issued Jul. 4, 2017, which is a 371 International Application of PCT/US14/027817 filed Mar. 14, 2014, which claims priority to U.S. Provisional Application Ser. No. 61/786,030, filed under 35 U.S.C. § 111(b) on Mar. 14, 2013, the disclosure of which is incorporated herein by reference in its entirety.

STATEMENT REGARDING FEDERALLY SPONSORED RESEARCH

The invention was made with no government support. The government has no rights in the invention.

TECHNICAL FIELD

The present disclosure relates to the field of compounds, compositions, and methods useful for the treatment or prevention of osteoporosis, osteoarthritis, metabolic bone disorders, fracture management, and other musculoskeletal disorders.

BACKGROUND OF THE INVENTION

Osteoporosis is a silent disease of bones that affects tens of millions of people over the age of 50. The disease results in decreased bone mineral density and ultimately bone fracture. Osteoporosis can lead to acute and chronic fractures, causing significant morbidity and mortality to patients. Other metabolic bone diseases can similarly result in weakened bones and fractures. Currently, the best medications available can reduce recurrent fracture risk only 65% of the time, and are associated with significant risks such as avascular necrosis of the tempormandibular joints, subtrochanteric femur fractures, and malignant bone tumors.

Osteoarthritis is the most common joint disorder in the world, and affects the majority of people over the age of 65. Osteoarthritis is a disease of cartilage and bone that results in the wearing away of the lining of the joint, and ultimately bone-on-bone changes. Osteoarthritis can lead to crippling joint pain and deformity, causing significant morbidity to patients. Currently, there are no medical treatments available to prevent or halt the progression of osteoarthritis. The standard of care for treating osteoarthritis dictates supportive pain management measures such as medications, physical therapy, braces, lifestyle changes, and activity modifications, until a patient can no longer tolerate the pain, at which point a joint fusion or replacement may be performed.

It would be advantageous to develop effective ways of preventing or treating osteoporosis, osteoarthritis, metabolic bone disorders, fracture management, and other musculoskeletal disorders.

SUMMARY OF THE INVENTION

Provided herein are analogs of PPARδ and 20-hydroxy prostaglandin $E_2$ (20-OH-$PGE_2$).

Provided herein is a method of treating patients, the method comprising treating mammalian stem cells with an effective amount of one or more of a PPARδ agonist and a 20-OH-$PGE_2$ antagonist, whereby the mammalian stem cells differentiate into a cell of osteoblast or chondroblast lineage In certain embodiments, the PPARδ agonist comprises the structural formula of Formula I:

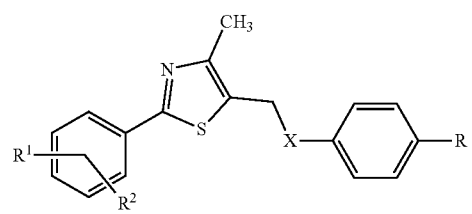

Formula I wherein X is O, S, NH, $NCH_3$, $NCH_2CH_3$, $NCH_2CH_2CH_3$ or $NCH(CH_3)_2$; R is $OCH_2R^3$, $CH=CHR^3$, or $(CH_2)_nR^3$, where n is 0, 1, 2, or 3 and $R^3$ is carboxylic acid, sulfonic acid, an acidic sulfonamide, or pharmacophoric mimics thereof; $R^1$ is H, $CH_3$, or $CF_3$; and $R^2$ is H, alkyl, substituted alkyl, or halogen; and salts, isomers, stereoisomers, enantiomers, racemates, solvates, hydrates, polymorphs, and prodrugs thereof. In particular embodiments, X is NH.

In certain embodiments, the PPARδ agonist has the structural formula of Formula I-A:

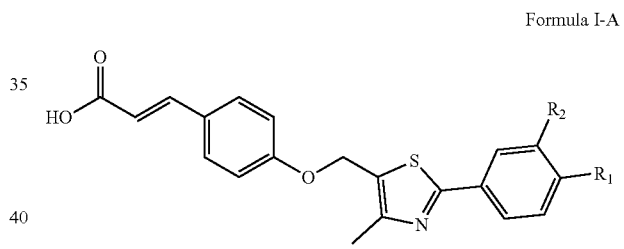

Formula I-A wherein $R_1$ is hydrogen and $R_2$ is $CF_3$.

In certain embodiments, the 20-OH-$PGE_2$ antagonist comprises the structural formula of Formula II:

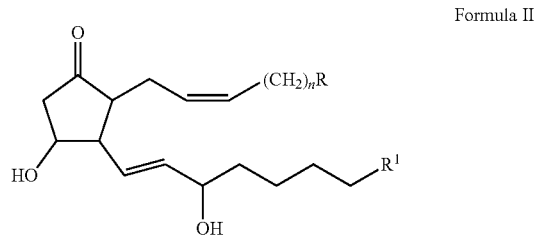

Formula II wherein R is carboxylic acid, sulfonic acid, an acidic sulfonamide, or pharmacophoric mimics thereof; $R^1$ is H, $CH_3$, OH, $CH_2OH$; and n is 1, 2, or 3; and salts, isomers, stereoisomers, enantiomers, racemates, solvates, hydrates, polymorphs, and prodrugs thereof.

In certain embodiments, the stem cells are present in a mammalian subject. In certain embodiments, the stem cells are isolated stem cells, and the method further comprises the step of administering the treated mammalian stem cells to a mammal in need thereof.

Further provided herein is a compound having the structural formula of Formula I:

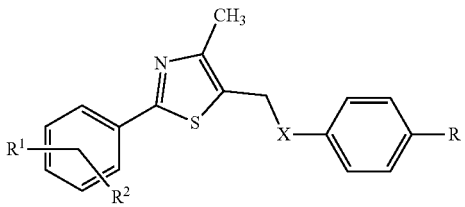

wherein X is O, S, or NH; R is $OCH_2R^3$, $CH=CHR^3$, or $(CH_2)_nR^3$, where n is 0, 1, 2, or 3 and $R^3$ is carboxylic acid, sulfonic acid, an acidic sulfonamide, or pharmacophoric mimics thereof; $R^1$ is H, $CH_3$, or $CF_3$; and $R^2$ is H, alkyl, substituted alkyl, or halide; provided that when R is $OCH_2CO_2H$, (i) either $R^1$ is not para-$CF_3$ or $R^2$ is not H, and (ii) either $R^1$ is not meta-$CH_3$ or $R^2$ is not para-tert-butyl. Further provided are salts, isomers, stereoisomers, enantiomers, racemates, solvates, hydrates, polymorphs, and prodrugs thereof. In certain embodiments, X is NH.

In certain embodiments, the compound has the structural formula of Formula I-A:

Formula I-A

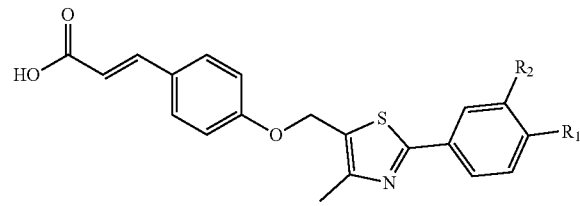

wherein $R_1$ is hydrogen, and $R_2$ is $CF_3$.

Further provided herein is a compound having the structural formula of Formula II:

Formula II

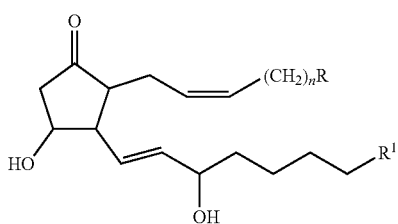

wherein R is carboxylic acid, sulfonic acid, an acidic sulfonamide, or pharmacophoric mimics thereof; $R^1$ is H, $CH_3$, OH, $CH_2OH$; and n is 1, 2, or 3; provided that when R is $CO_2H$, either $R^1$ is not $CH_2OH$ or n is not 3. Further provided are salts, isomers, stereoisomers, enantiomers, racemates, solvates, hydrates, polymorphs, and prodrugs thereof.

Further provided is a pharmaceutical composition comprising a compound described herein and a pharmaceutically acceptable carrier, excipient, diluent, or adjuvant. In certain embodiments, the compound is present at a concentration ranging from about 0.1 µM to about 1 µM.

Further provided is a method of treating, ameliorating, or prevent osteoarthritis, osteoporosis, or metabolic bone disease, the method comprising administering an effective amount of the pharmaceutical composition described herein to a patient in need thereof.

Further provided is a method of treating, ameliorating, or preventing osteoarthritis, osteoporosis, or metabolic bone disease, the method comprising treating isolated stem cells with the pharmaceutical composition described herein, and administering the treated stem cells to a patient in need thereof to treat, ameliorate, or prevent osteoarthritis, osteoporosis, or metabolic bone disease.

Further provided is a kit for preparing a pharmaceutical composition comprising a first container housing one or more of a PPARδ agonist or a 20-OH-$PGE_2$ antagonist; and a second container housing a pharmaceutically acceptable carrier, excipient, diluent, or adjuvant. In certain embodiments, the kit further comprises a syringe configured to inject a pharmaceutical composition. In certain embodiments, the kit comprises both a PPARδ agonist and a 20-OH-$PGE_2$ antagonist.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

(FIG. 2A.) Adipogenesis was measured as the relative absorbance of Oil Red O at day 14 after inducing adipogenesis. (FIG. 2B.) Mean±SE, *P<0.05 versus vehicle.

FIGS. 4A-4B: Effect of 20-HETE on adipogenesis in the presence and absence of COX-1 inhibitor, COX-2 inhibitor, and the $PGE_2$ synthase inhibitor (CAY10526). (FIG. 4A.) Adipogenesis was measured as the relative absorbance of Oil Red O at day 14 after inducing adipogenesis. (FIG. 4B.) Mean±SE, *P<0.05 versus vehicle, #P<0.05 versus control.

(FIG. 5A.) Adipogenesis was measured as the relative absorbance of Oil Red O at day 14 after inducing adipogenesis. (FIG. 5B.) Mean±SE, *P<0.05 versus vehicle, #P<0.05 versus control.

(FIG. 7A.) Expression of PPARγ (FIG. 7B), Mest (FIG. 7C), and β-catenin (FIG. 7D) was determined by Western blot analysis in MSC-derived adipocytes. Quantitative densitometry evaluation of the proteins ratio was determined. Data are expressed as means±SE, *P<0.05 versus corresponding conditions without 20-OH-PGE$_2$.

DETAILED DESCRIPTION OF THE INVENTION

Figure 1A:
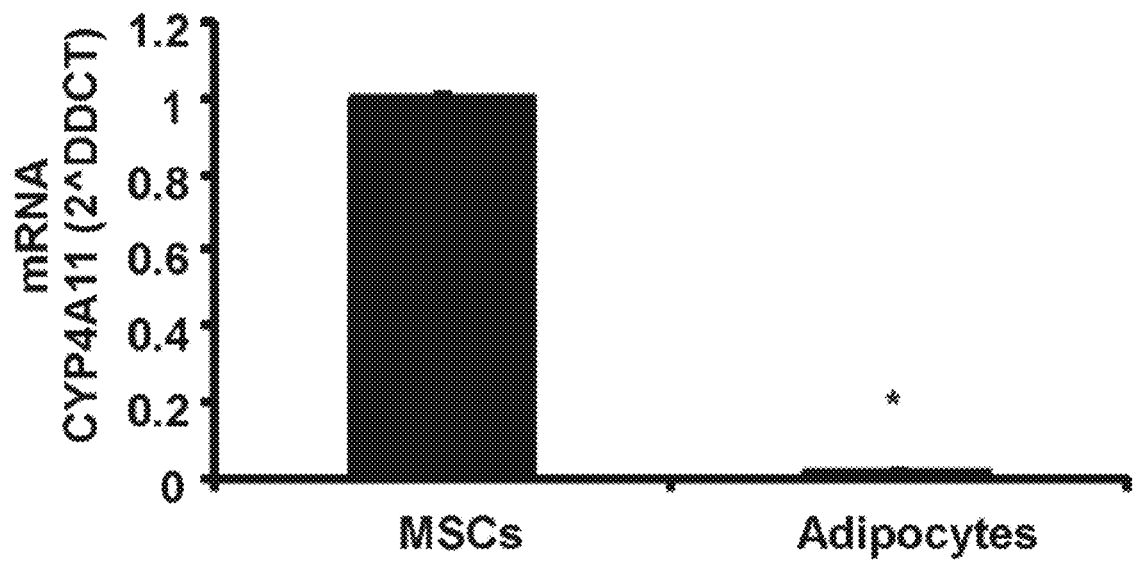
FIGS. 1A-1C: Levels of mRNA for Cyp4F11 (FIG. 1A) and Cyp4F2 (FIG. 1B), and levels of $PGE_2$ in mesenchymal stem cells (MSC) (FIG. 1C) before and after adipogenic differentiation (adipocytes). The data are expressed as means±SE. *P<0.05 versus MSC; #P<0.05 versus vehicle; 'P<0.05 versus COX-1 or COX-2 inhibitor.

Various embodiments are described herein in the context of PPARδ and 20-OH-PGE$_2$ analogues, and methods of using the same. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skill in the art having the benefit of this disclosure.

Definitions

The term "PPAR" refers to Peroxisome Proliferator Activated Receptors, which are orphan receptors belonging to the steroid/retinoid receptor superfamily of ligand-activated transcription factors. Three mammalian PPARs have been identified, termed PPARα, PPARγ, and PPARδ. PPARs regulate expression of target genes by binding to DNA response elements as heterodimers with the retinoid X receptor.

The term "pharmacophoric mimic" refers to a compound or functional group having the steric and electronic features necessary for molecular recognition by a biological macromolecule similar to that of another compound or functional group.

The term "alkyl" as used herein refers to monovalent alkyl groups, which are saturated hydrocarbons, preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

Unless stereochemistry is specifically indicated, all stereoisomers of the compounds herein are included, as pure compounds as well as mixtures thereof.

Some of the crystalline forms for the compounds may exist as polymorphs and as such are included. In addition, some of the compounds herein may form solvates with water (i.e., hydrates) or common organic solvents, which are also included.

Protected forms of the compounds herein are further included. A variety of protecting groups are possible.

Prodrugs of the compounds herein are included. In general, such prodrugs are functional derivatives of the compounds that are readily convertible in vivo into the required compound. Thus, in the methods of treatment, the term "administering" includes the treatment of the various disorders described with the compound specifically disclosed or with a compound which may not be specifically disclosed, but which converts to the specified compound in vivo after administration to a subject in need thereof. A simple example of a prodrug, not meant to be limiting in any manner, would be an alkyl ester of the acidic groups container at R$^3$ within Formula I or at R within Formula II.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs." The term "hydrate" refers to a solvate with water.

The term "racemate" refers to a mixture that contains an equal amount of enantiomers.

It will be appreciated by one of ordinary skill in the art that asymmetric centers may exist in any of the compounds disclosed herein. Thus, the compounds may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will also be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents.

General Description

Mesenchymal stem cells are stem cells that can develop into connective tissue throughout the body, such as bone, fat, and cartilage. The present disclosure is aimed at directing mesenchymal stem cells toward osteogenesis or chondrogenesis as opposed to adipogenesis, thereby inducing bone formation over fat formation. The compounds, compositions, and methods described herein are thus useful in the treatment and/or prevention of musculoskeletal disorders such as osteoporosis, osteoarthritis, metabolic and bone disease, as well as for fracture management and prosthetic integration.

Further provided herein is a method of inducing osteogenesis, the method comprising: contacting a mammalian cell with an effective amount of at least one pharmaceutical composition described herein, whereby the mammalian cell differentiates into a cell of an osteoblast lineage, or whereby the mammalian cell differentiates into a cell of a chondroblast lineage.

In certain embodiments, the mammalian cell is an in vivo mammalian cell.

In certain embodiments, the mammalian cell is a mesenchymal stem cell.

In certain embodiments, the stem cell is isolated from a primate.

In certain embodiments, the primate is a human.

In certain embodiments, the step of contacting is by oral administration of the compound to the mammal.

In certain embodiments, the step of contacting is by intravenous administration of the compound to the mammal.

In certain embodiments the step of contacting is by subcutaneous administration of the compound to the mammal.

In certain embodiments, the method further comprises detecting differentiation of the mammalian cell into an osteocyte cell of an osteoblast lineage.

In certain embodiments, the method further comprises detecting differentiation of the mammalian cell into a chondrocyte cell of a chondroblast lineage.

In certain embodiments, wherein the mammalian cell is attached to a solid support.

In certain embodiments, the solid support is a three dimensional matrix.

In certain embodiments, the solid support is a planar surface.

Further provided herein is a method of treating a bone disorder, comprising: contacting a mammalian cell with a pharmaceutical composition as described herein, whereby the mammalian cell differentiates into a cell of an osteoblast lineage, wherein the bone disorder is associated with defective osteoblasts.

In certain embodiments, the bone disorder is osteoporosis.

In certain embodiments, the method further comprises administering the cell of an osteoblast lineage to an individual with the disorder, thereby treating the disorder.

In certain embodiments, the administration is by surgical implantation.

Further provided herein is a method of treating a cartilage disorder, comprising: contacting a mammalian cell with a pharmaceutical composition as described herein, whereby the mammalian cell differentiates into a cell of a chondroblast lineage, wherein the bone disorder is associated with defective chondroblasts.

In certain embodiments, the cartilage disorder is one or more of: injury to articular cartilage; osteoarthritis; costochondritis; herniation; achondroplasia; relapsing polychondritis; benign or non-cancerous chondroma; and, malignant or cancerous chondrosarcoma.

Further provided herein is a method for inducing chondrogenesis leading to cartilage formation or chondrogenesis leading to cartilage formation that further mediates formation of new bone tissue in a vertebrate, the method comprising administering a therapeutically effective amount of a pharmaceutical composition as described herein to the vertebrate.

In certain embodiments, the administration is local or systemic.

Further provided herein is a method for promoting chondrogenesis at a site of skeletal surgery in a vertebrate, the method comprising delivering a pharmaceutical composition as described herein at the site of skeletal surgery wherein such delivery induces chondrogenesis leading to cartilage formation at the site or chondrogenesis leading to cartilage formation that further mediates formation of new bone tissue at the site.

In accordance with the present disclosure, there are provided herein compounds that are analogs of PPARδ and 20-OH-PGE$_2$. The analog compounds serve as either agonists to compounds that promote bone formation or antagonists to compounds that induce adipogenesis.

The first group of compounds provided herein, PPARδ affinity ligand analogs, have the structural formula of Formula I:

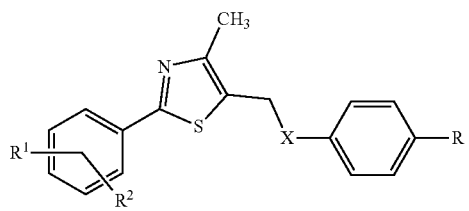

Formula I wherein X is O, S, NH, NCH$_3$, NCH$_2$CH$_3$, NCH$_2$CH$_2$CH$_3$ or NCH(CH$_3$)$_2$; R is OCH$_2$R$^3$, CH=CHR$^3$, or (CH$_2$)$_n$R$^3$, where n is 0, 1, 2, or 3 and R$^3$ is carboxylic acid, sulfonic acid, an acidic sulfonamide, or pharmacophoric mimics thereof; R$^1$ is H, CH$_3$, or CF$_3$; and R$^2$ is H, alkyl, substituted alkyl, or halide; provided that when R is OCH$_2$CO$_2$H, (i) either R$^1$ is not para-CF$_3$ or R$^2$ is not H, and (ii) either R$^1$ is not meta-CH$_3$ or R$^2$ is not para-tert-butyl. Also provided are salts, isomers, stereoisomers, enantiomers, racemates, solvates, hydrates, polymorphs, and prodrugs of Formula I.

PPARδ is a nuclear receptor protein that functions as a transcription factor regulating the expression of genes. PPARδ plays a vital role in the regulation of cellular differentiation and metabolism. For example, PPARδ activates fat metabolism to prevent obesity. The analogs encompassed by Formula I, some of which serve as PPARδ agonists, also inhibit adipogenesis and stimulate fat metabolism to prevent obesity. Provided herein are methods of increasing bone density involving administering the PPARδ agonist compounds described.

Figure 15:
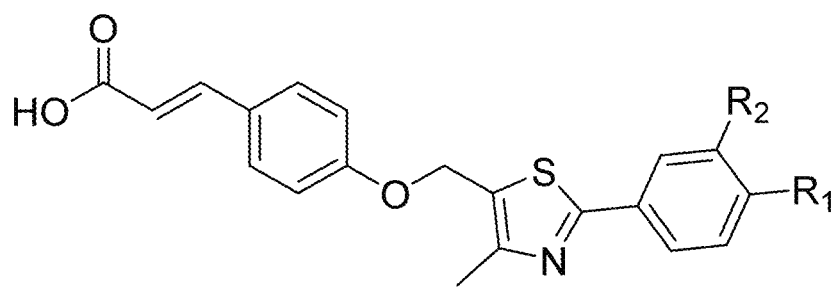
FIG. 15: Table 1, showing the differential effects on stem cells when treated with GW0742 and compounds 6a-6c.

In certain instances, the compounds of Formula I are also, or alternatively, PPARγ agonists. In certain other instances, the compounds of Formula I are both PPARδ agonists and PPARγ agonists. The compounds of Formula I have a structure-activity relationship (SAR) that demonstrates the importance of the substitution pattern on the phenyl ring having the R group. The addition of a trifluoromethyl group to either the para- or meta-position of this phenyl ring endows selectivity for PPARδ over PPARγ, as compared to the molecule having no substitution in this location. (FIG. 15.) This is distinguishable from the data in the literature, and indicates that the meta-CF$_3$ group is a uniquely preferred embodiment within this specific SAR series.

Figure 12:
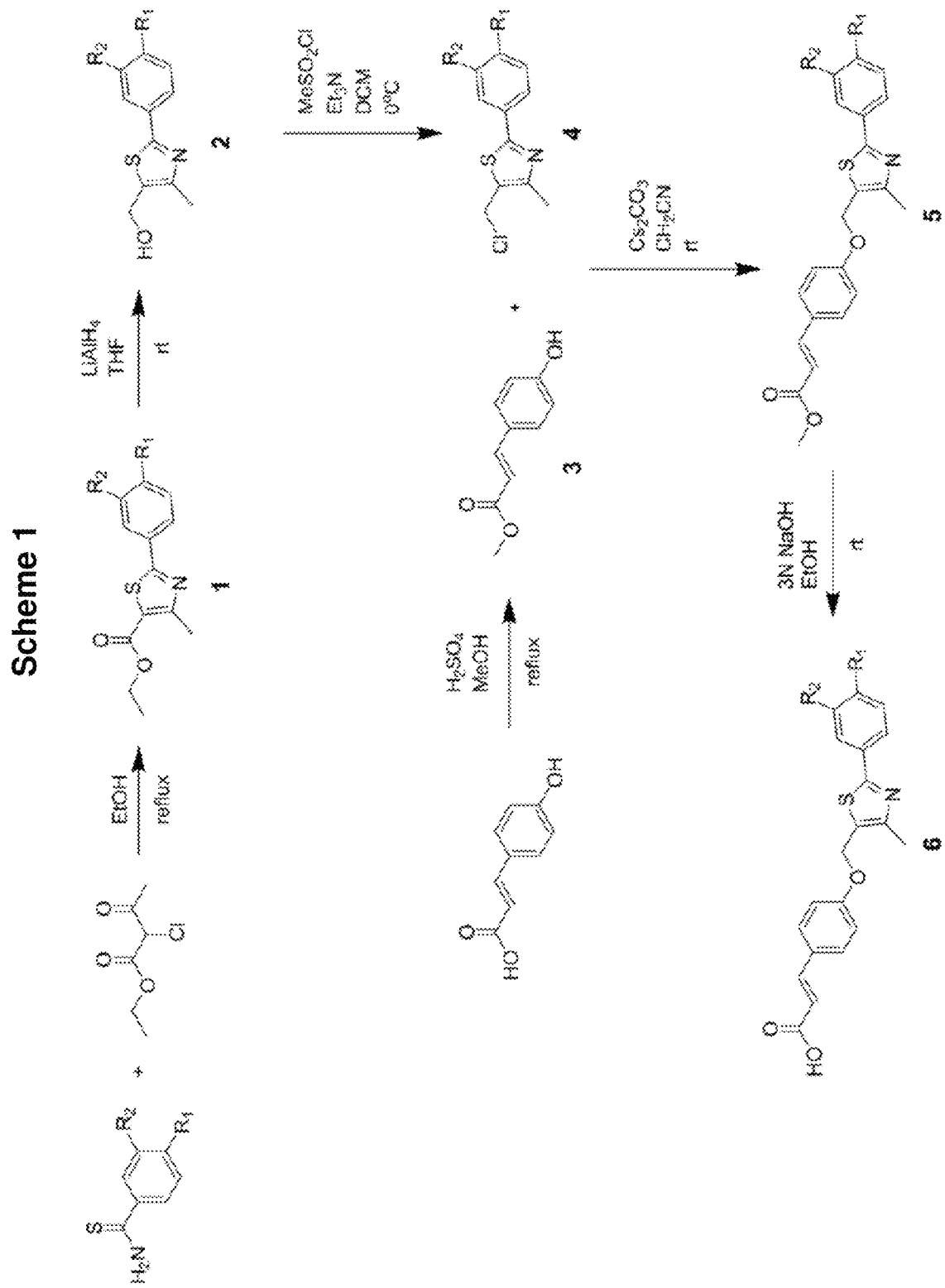
FIG. 12: Scheme 1, showing a non-limiting example of a synthetic route to produce compounds 6a-6c, wherein R$_1$ is H, CF$_3$, or CH$_3$; R$_2$ is H, CF$_3$, alkyl, or substituted alkyl.
Figure 13:
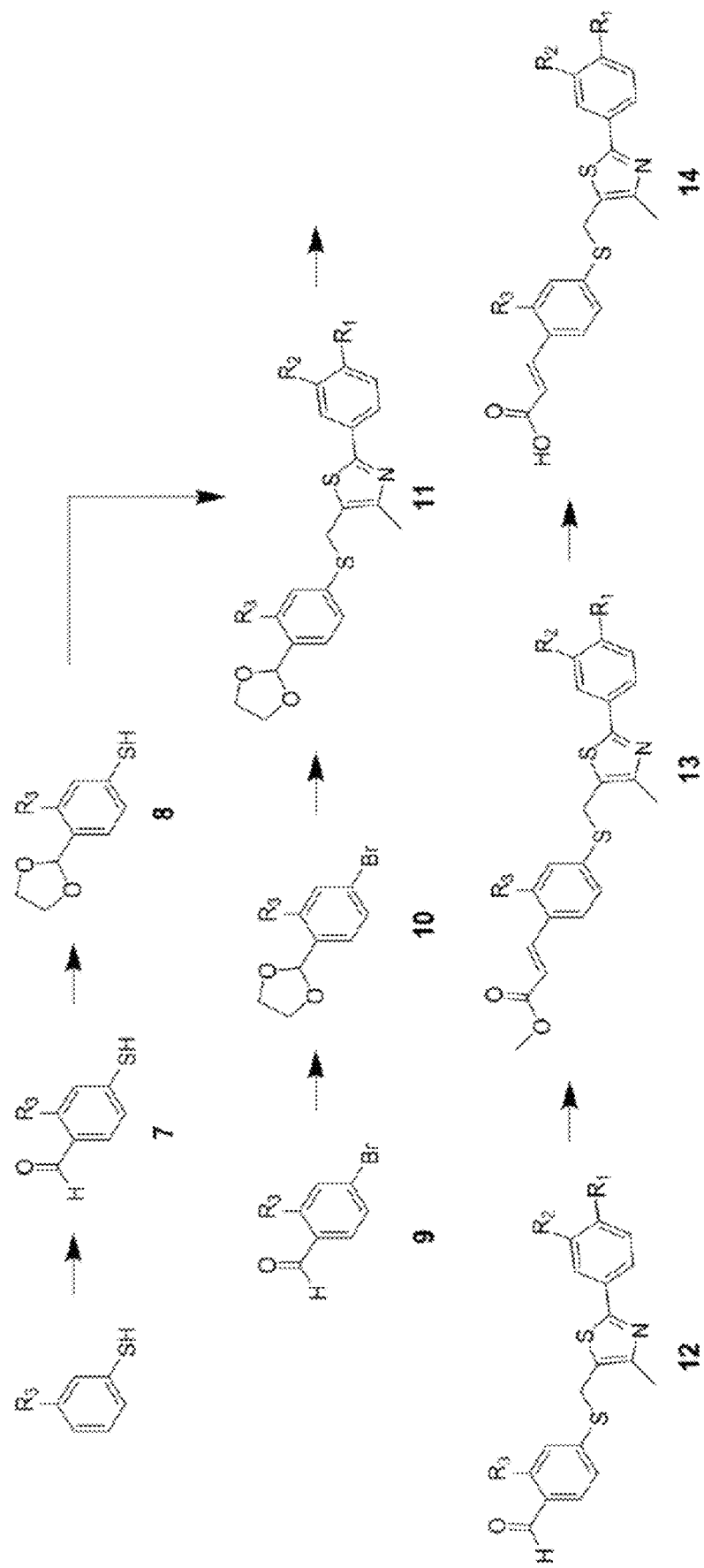
FIG. 13: Scheme 2, showing a non-limiting example of a synthetic route to produce various PPARδ agonist analogs, wherein R$_1$ is H, CF$_3$, or CH$_3$; R$_2$ is H, CF$_3$, alkyl, or substituted alkyl; R$_3$ is H, CF$_3$, alkyl, or substituted alkyl.

Scheme 1 and Scheme 2, shown in FIG. 12 and FIG. 13, respectively, illustrate non-limiting examples of synthetic routes to produce PPARδ agonists. Within this group of compounds are described compounds 6a, 6b, and 6c. These analogs have the structural formula shown below as Formula I-A.

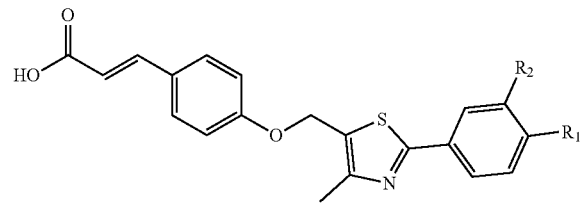

Formula I-A

Compound 6a has the structural formula of Formula I-A, where R$_1$ and R$_2$ are each hydrogen. Compound 6b has the structural formula of Formula I-A, where R$_1$ is CF$_3$ and R$_2$ is hydrogen. Compound 6c has the structural formula of Formula I-A, where R$_1$ is hydrogen and R$_2$ is CF$_3$.

By way of a non-limiting example, compounds 6a-6c can be prepared via the synthetic route shown in Scheme 1, FIG. 12. To begin, a carboxylic acid ethyl ester 1 is prepared by adding a chloroacetoacetate to a thiobenzamide. Then, LiAlH$_4$ in THF is added to the carboxylic acid ethyl ester 1 to yield a thiazole alcohol 2. Triethylamine is added to the thiazolemethanol 2 in anhydrous dichloromethane, and to the resulting mixture is added methanesulfonyl chloride. The purified product is a thiazole 4. A hydroxycinnamic acid methyl ester 3 is prepared by adding sulfuric acid to p-coumaric acid in anhydrous methanol. To a solution of the ester 3 and the thiazole 4 is added cesium carbonate. The product is a methyl ester 5. NaOH is added to the methyl ester 5 to yield compound 6, wherein R$_1$ is H, CF$_3$, or CH$_3$, and R$_2$ is H, CF$_3$, alkyl, or substituted alkyl.

The second group of compounds provided herein, 20-OH-PGE$_2$ analogs, have the structural formula of Formula II:

Formula II

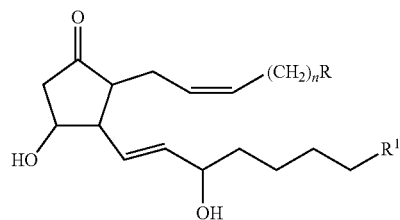

wherein R is carboxylic acid, sulfonic acid, an acidic sulfonamide, or pharmacophoric mimics thereof; R$^1$ is H, CH$_3$, OH, CH$_2$OH; and n is 1, 2, or 3; provided that when R is CO$_2$H, either R$^1$ is not CH$_2$OH or n is not 3. Further provided are salts, isomers, stereoisomers, enantiomers, racemates, solvates, hydrates, polymorphs, and prodrugs of Formula II. Compounds of Formula II are 20-OH-PGE$_2$ antagonists.

The significance of 20-OH-PGE$_2$ antagonists begins with 20-hydroxy-5,8,11,14-eicosatetraenoic acid (20-HETE), which is synthesized by P450 (CYP)-catalyzed ω-hydroxylation of arachidonic acid. 20-HETE is a primary eicosanoid in the microcirculation that plays a role in the regulation of vascular tone and renal tubular homeostasis. 20-HETE has been shown to stimulate the production of superoxides and inflammatory cytokines, as well as inhibit endothelial eNOS and increase oxidative stress. 20-HETE thus plays a role in the regulation of adipose tissue.

20-HETE induces oxidative stress and is associated with increased body mass index (BMI) and the metabolic syndrome. 20-HETE has also been shown to mediate cellular proliferation, angiogenesis, and inflammation, all of which may materially contribute to the process of adipogenesis. 20-HETE is metabolized by the cyclooxygenase (COX) pathway—the rate-limiting enzyme that catalyzes the conversion of arachidonic acid into prostaglandins—into 20-OH-endoperoxides and consequently into 20-OH-PGE$_2$. 20-OH-PGE$_2$, as shown by the examples described below, is a potent inducer of adipogocity. The compounds of Formula II, which are antagonists of 20-OH-PGE$_2$, thus serve to prevent the inducement of adipogenesis and thereby stimulate bone formation through osteogenesis or cartilage formation through chondrogenesis.

Figure 14:
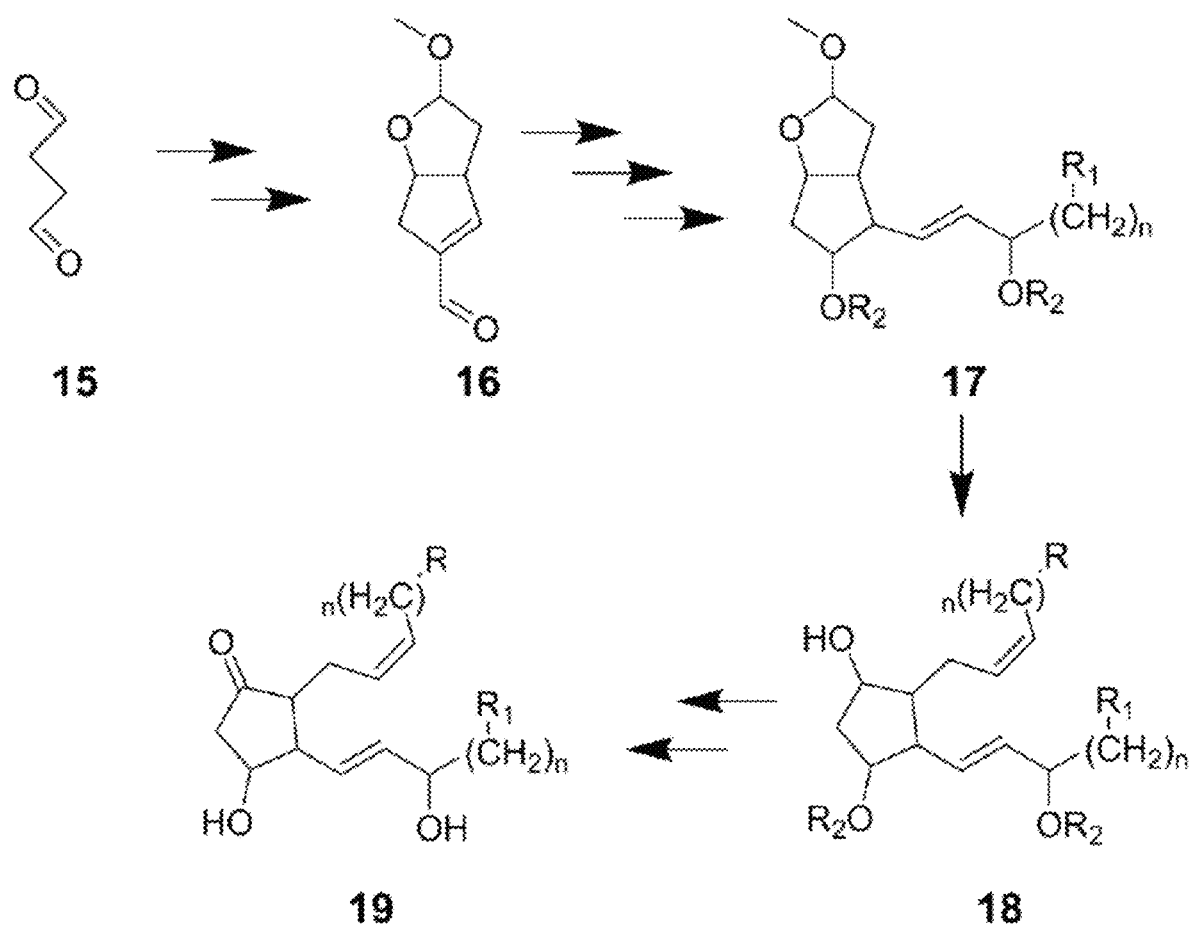
FIG. 14: Scheme 3, showing a short synthesis of 20-OH-PGE$_2$ analogs, where R is carboxylic acid, sulfonic acid, or acidic sulfonamide, or pharmacophoric mimics thereof; R$_1$ is H, CH$_3$, OH, or CH$_2$OH; n is 1, 2, or 3; and R$_2$ is a suitable hydroxyl protecting group that allows for simultaneous removal as the final step. An alternative, 17-step synthesis of these compounds is also possible.

Scheme 3, shown in FIG. 14, illustrates a shortened synthetic route for producing 20-OH-PGE$_2$ antagonists. Alternatively, a longer, 17-step synthesis of these compounds is possible.

It is intended that any of the compounds disclosed herein could be used in a medication, a food additive, an injection, or a surgical implant designed to treat, ameliorate, or modify, osteoporosis, osteoarthritis, metabolic bone disease, and/or fracture management problems. The compounds of the present disclosure could be used to enhance the natural pathways to direct a patient's own mesenchymal stem cells toward bone and cartilage formation over adipose formation, thereby preventing and/or treating these underlying conditions. The compounds could also be incorporated into a pharmaceutical composition, or could be used to treat isolated stem cells that are then administered to a patient in need thereof.

Pharmaceutical Compositions

Pharmaceutical compositions of the present disclosure comprise an effective amount of a compound disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In most cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits

It is further intended the compounds disclosed herein could be packaged in the form of a kit containing a single or separate containers. Many embodiments of such kits are possible. For instance, a kit could house two containers, the first container comprising a compound of Formula I, and the second container comprising a compound of Formula II. By way of further non-limiting example, a kit could have a first container housing a solution comprising one or more compounds of Formula I and Formula II, and a second container comprising a syringe configured to inject the solution. As another example, a kit for the preparation of a pharmaceutical composition could have a first container housing one or more compounds of Formula I and Formula II, and a second container housing a pharmaceutically acceptable carrier, excipient, diluent, or adjuvant. Many other variations and embodiments of such kits are envisioned. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1—Differential Effects of 20-OH-PGE$_2$ and 20-HETE on Adipogenesis

Frozen bone marrow mononuclear cells were purchased from Allcells (Emeryville, Calif.). After thawing, mononuclear cells were resuspended in an α-minimal essential medium (α-MEM, Invitrogen, Carlsbad, Calif.) supplemented with 10% heat inactivated fetal bovine serum (FBS, Invitrogen) and 1% antibiotics and antimycotic (Invitrogen). The cells were plated at a density of 1-5×10$^6$ cells per 100 cm$^2$ dish. The cultures were maintained at 37° C. in a 5% CO$_2$ incubator. The medium was changed after 48 hours and every 3-4 days thereafter. When the mesenchymal stem cells (MSCs) were confluent, the cells were recovered by the addition of 0.25% trypsin/EDTA (Invitrogen). MSCs were plated in either a 75 cm$^2$ flask or a 24-well plate and cultured in a α-MEM with 20% FBS up to a density of 2.0×10$^4$ cells/cm$^2$. The medium was replaced with adipogenic medium, and the cells were cultured for an additional 14 days. The adipogenic media consisted of complete culture medium supplemented with DMEM-high glucose, 10% (v/v) FBS, 10 μg/mL insulin, 0.5 mM dexamethasone (Sigma-Aldrich, St. Louis, Mo.), and 1% antibiotics and antimycotic (Invitrogen) in the presence and absence of the COX-1 inhibitor (2-valeryloxybenzoic acid, Cayman, Ann Arbor, Mich.) and the COX-2 inhibitor (3-(4-methylsulphonylphenyl)-4-phenyl-5-trifluoromethylisoxazol, Cayman) with and without 20-HETE, 20-HETE agonist (20-5,14-HEDE), or 20-OH-PGE$_2$. 20-HETE, 20-HETE agonist, and 20-OH-PGE$_2$ were added three times a week at concentrations of 0.1 μM and 1 μM. Inhibitors of COX-1 and COX-2 were added three times a week at a dose of 100 μM and 5 μM, respectively.

At day 14 of adipogenesis, 0.21% Oil Red O in 100% isopropanol (Sigma-Aldrich) was used. Briefly, adipocytes were fixed in 10% formaldehyde, washed in Oil Red O for 10 minutes, and rinsed with 60% isopropanol (Sigma-Aldrich). The Oil Red O was then eluted by adding 100% isopropanol for 10 minutes, and OD was measured at 490 nm for 0.5 s reading. MSC-derived adipocytes were measured by Oil Red O staining (OD=490 nm) after day 14. Each value of Oil Red O staining was normalized by cell numbers (values at OD=490 nm).

Lipid droplets were measured using an ImagePro Analyzer (Media Cybernetics Corporation, Silver Springs, Md.). The MSC-derived adipocytes were treated with increasing concentration of 20-OH-PGE$_2$ (1-1,000 nM) every alternate day for 14 days. To quantify the number and size of the lipid droplets in these images, a proprietary algorithm was developed that segments circular staining patterns. The algorithm was then applied to images obtained from the lipid optical channel for cells exposed to different doses of 20-OH-PGE$_2$.

Total RNA was isolated using the RNeasy mini kit (Qiagen, Valencia, Calif.) according to the manufacturer's instructions. First-strand cDNA was synthesized with Roche reverse transcription reagents. Total RNA (0.5-1 μg) was analyzed by real-time PCR. The quantitative real-time polymerase chain reaction (qRT-PCR) was performed with the TaqMan gene expression assay on an Applied Biosystems 7500 fast real-time PCR system according to the manufacturer's recommended protocol (Applied Biosystems, Foster City, Calif.). Each reaction was run in triplicate. The comparative threshold cycle (CT) method was used to calculate the amplification fold as specified by the manufacturer.

Western blot analysis of adipocyte cell lysate was carried out. Cells were placed in a homogenization buffer, and homogenates were centrifuged at 27,000 g for 10 minutes at 4° C. The supernatant was used for the measurements of COX-1, COX-2, PPARγ, Mest, and β-catenin protein levels. The levels were quantified by scanning densitometry using an imaging densitometer, normalized to the levels of total protein.

PGE$_2$ levels were determined in the culture supernatant. Multiple assays were conducted for quantification of the proteins (AssayGate Inc., Ijamsville, Md.). All measurements were performed in triplicate.

Statistical significance between experimental groups was determined by the Fisher method of analysis of multiple comparisons (P<0.05 was regarded as significant). For comparison between treatment groups, the null hypothesis was tested by either a single-factor ANOVA for multiple groups or the unpaired t-test for two groups. Data are presented as mean±SEM. Differences between experimental groups were evaluated with ANOVA with Bonferroni corrections. Statistical significance was regarded as significant at P<0.05.

Figure 1B:
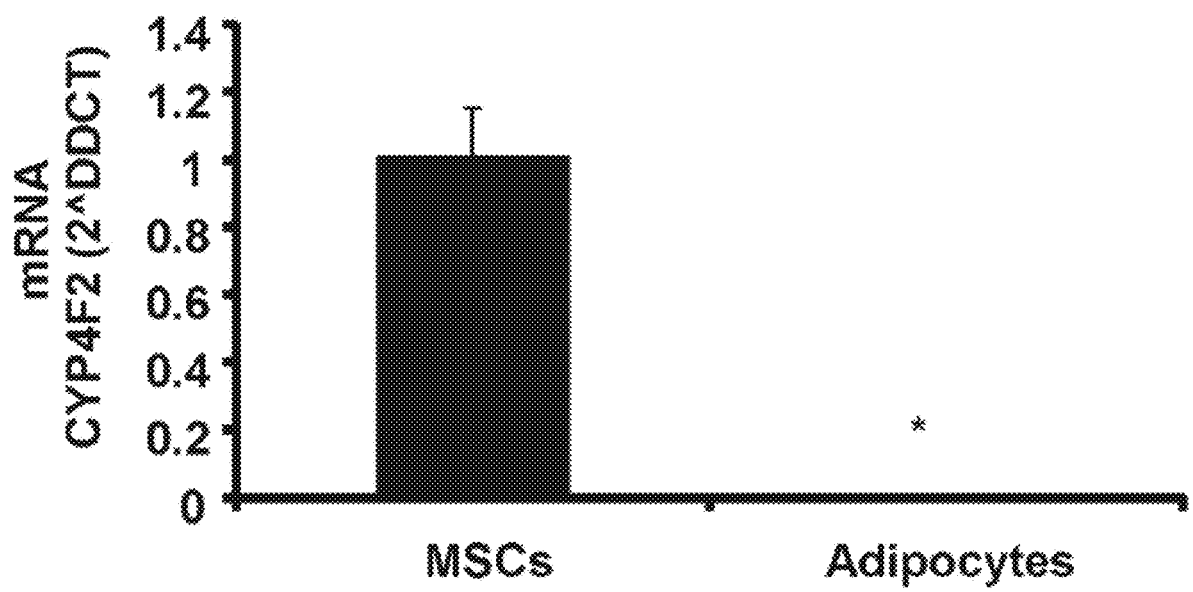
Figure 1C:
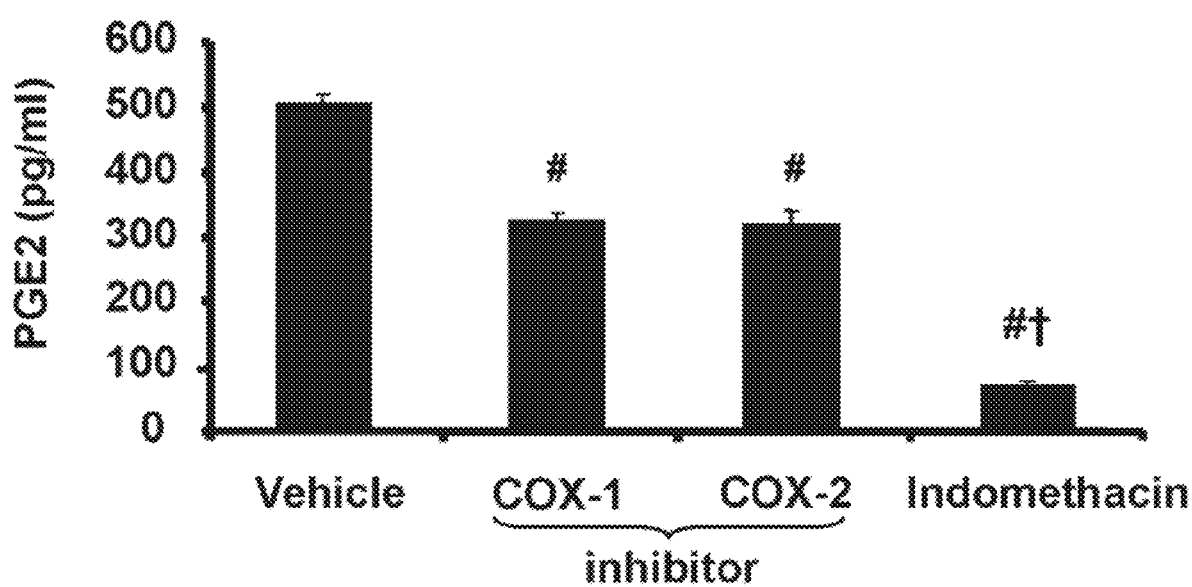

The expression levels of CYP4-ω-hydroxylases were determined in MSC before and before completion of adipogensis as shown in FIGS. 1A-1B. MSC expressed relatively high mRNA levels of CYP4A11 and CYP4F2 (the other major 20-HETE producing CYP-4-ω-hydroxylases in humans) before the start of adipogenic differentiation. In adipocytes derived from MSC, mRNA levels of these hydroxylases were nearly undetectable. To evaluate COX activity in MSC exposed to adipogenic environment, PGE$_2$ levels were determined in conditioned media (FIG. 1C). COX-1 and COX-2 inhibitors decreased PGE$_2$ levels compared with levels in the conditioned media without indomethacin. Addition of indomethacin, which is a dual COX-1 and COX-2 inhibitor, further decreased PGE$_2$ levels, as shown in FIG. 1C.

Figure 2A:
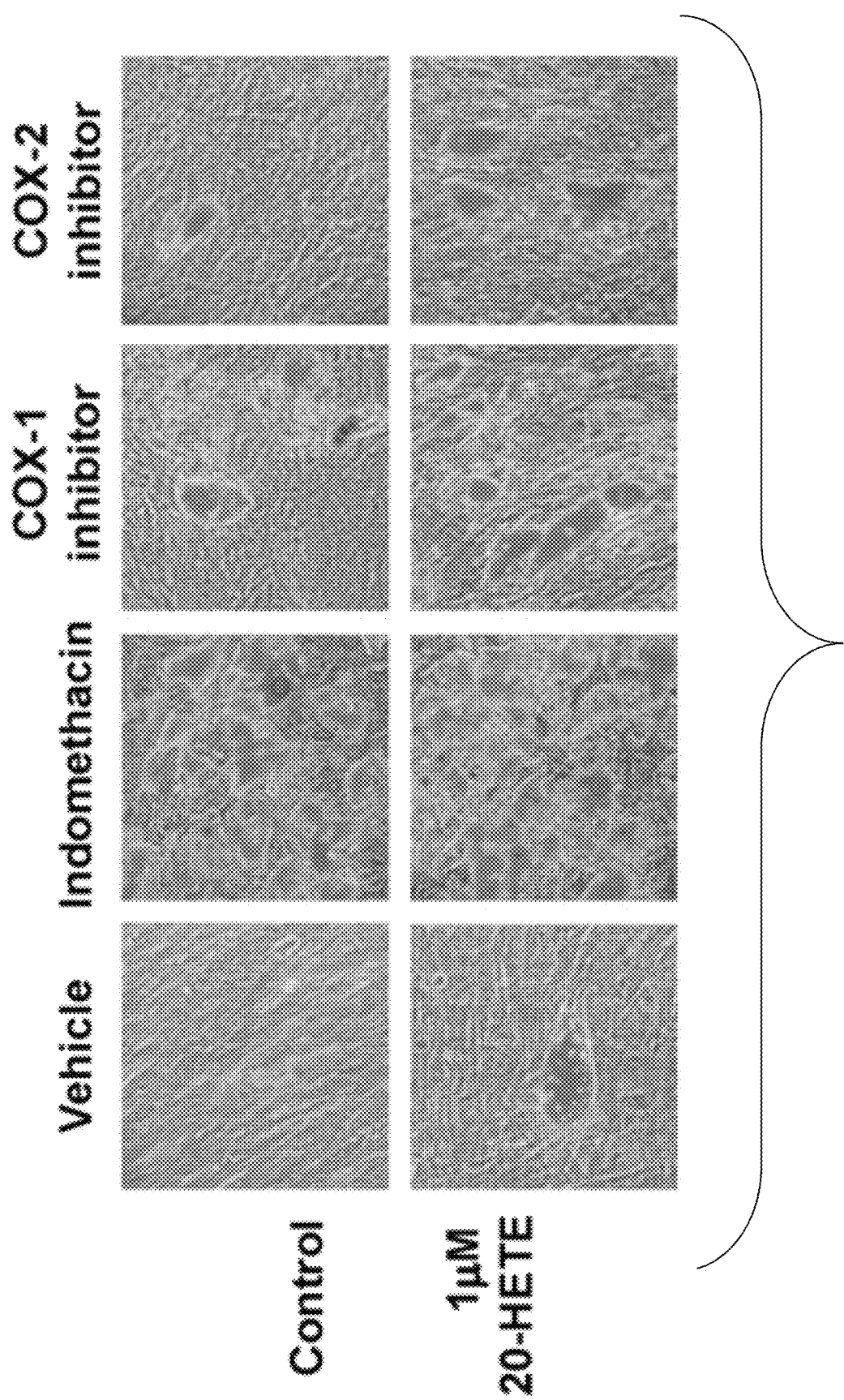
FIGS. 2A-2B: Effect of 20-HETE on adipogenesis in the presence and absence of indomethacin, COX-1 inhibitor (valeroyl salicylate), and COX-2 inhibitor (CAY10404).
Figure 2B:
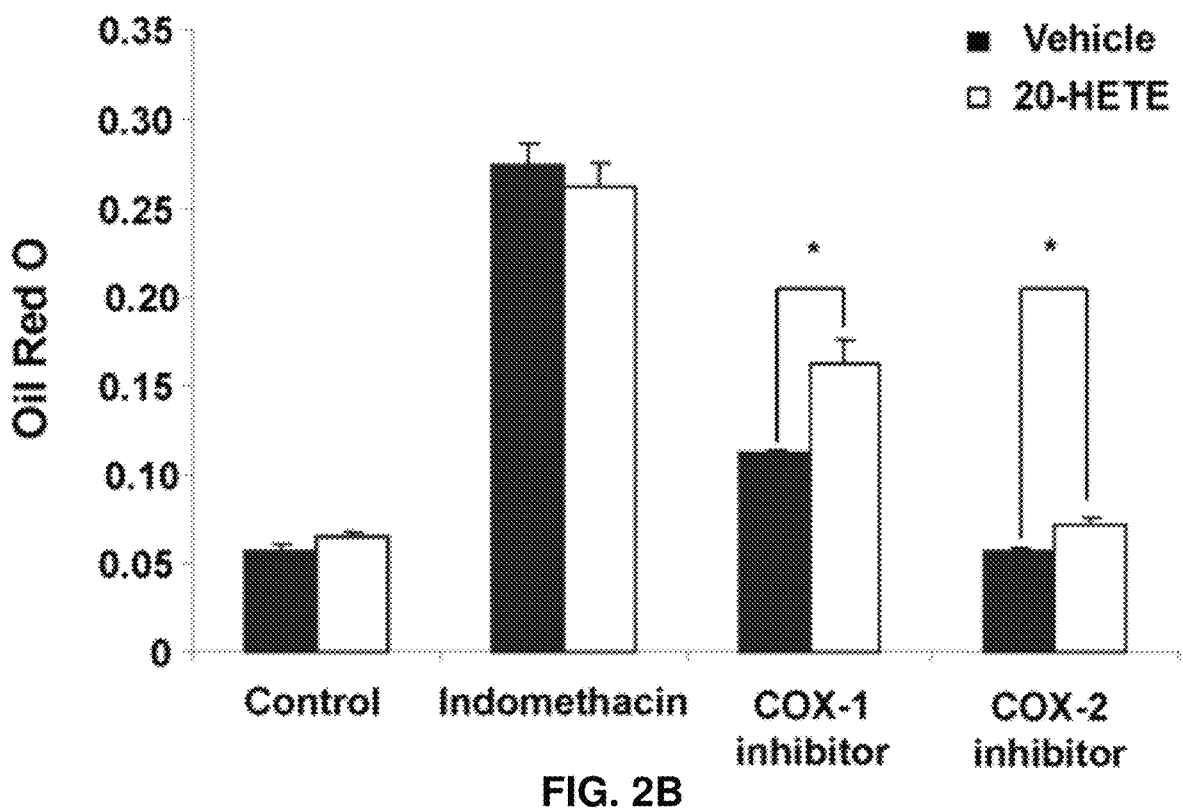
Figure 3:
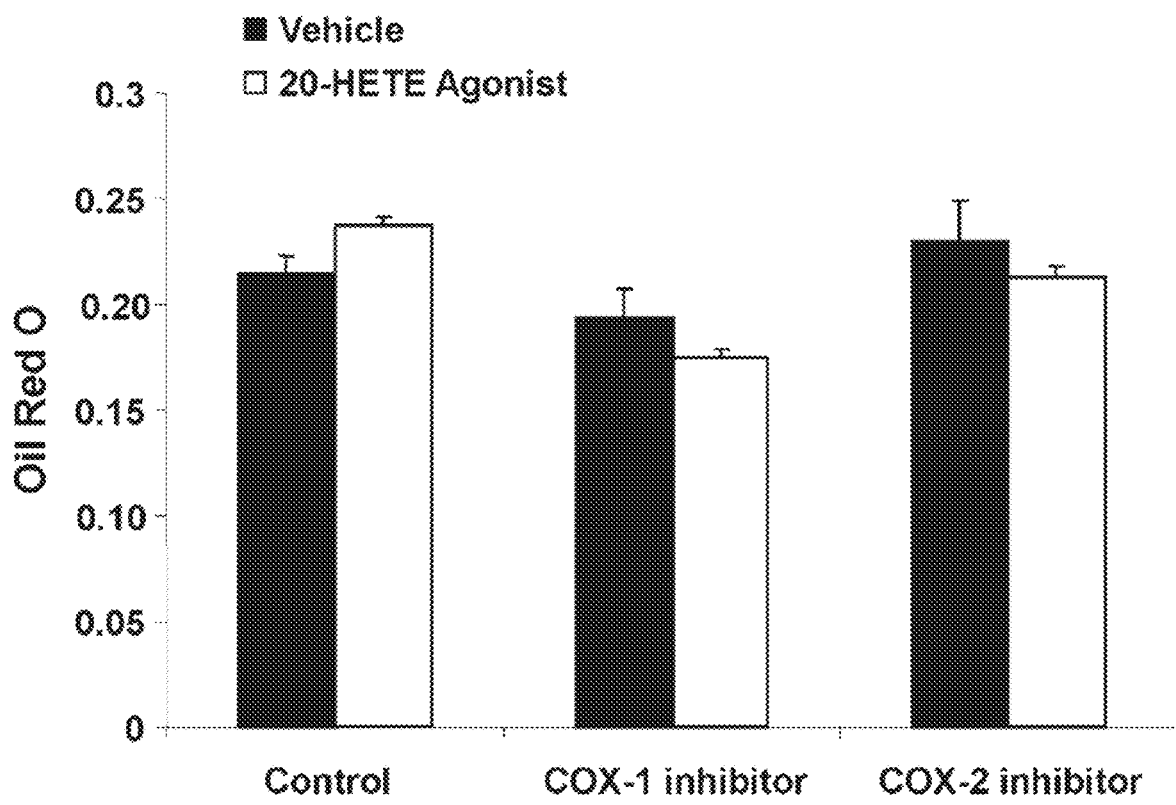
FIG. 3: Effect of 20-HETE agonist on adipogenesis in the presence and absence of COX-1 or COX-2 inhibitor. Adipogenesis was measured as the relative absorbance of Oil Red O at day 14 after inducing adipogenesis. Mean±SE.
Figure 4B:
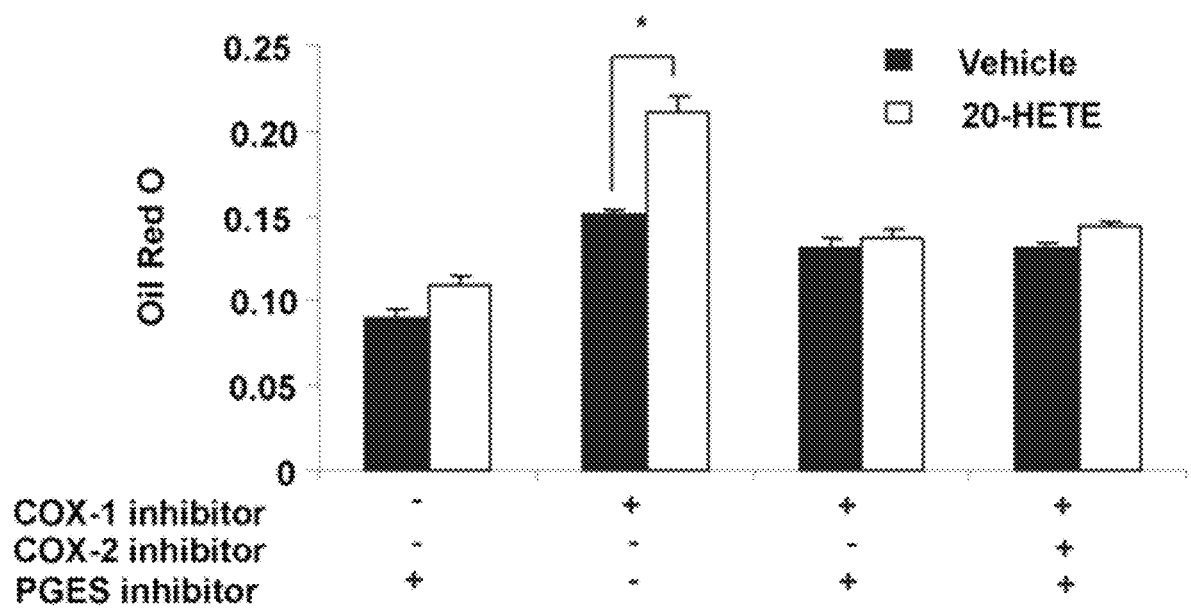

The effect of 20-HETE on lipid accumulation in MSC-derived adipocytes was examined in the presence and the absence of either a COX-1 inhibitor or a COX-2 inhibitor. As seen in FIGS. 2A-2B, 20-HETE enhanced lipid accumulation in cells exposed to a COX-1 inhibitor but not in cells exposed to COX-2 inhibitor. The absence of such an effect on 20-HETE in cells treated with a COX-2 inhibitor indicates that a COX-2-derived 20-HETE metabolic product plays a role in mediating these enhanced lipogenic effects. The direct effect of 20-HETE on lipid accumulation in MSCs derived adipocytes was further refuted by the inability of a 20-HETE agonist [sodium 2-((5Z,14Z-)-20-hydroxyicosa-5,14-dienamido) acetate, 20-HEDE] to mimic the effects of exogenous 20-HETE, as shown in FIG. 3. Results show that in the presence of COX-1 and COX-2 inhibitors, the 20-HETE agonist 20-HEDE had no significant effect on adipogenesis, thus further indicating that a COX-2-derived metabolic product has an enhanced adipogenic effect. Subsequently, addition of the microsomal PGE$_2$ synthase inhibitor CAY10526 abolished the adipogenic effect of 20-HETE in the presence of a COX-1 inhibitor, as shown in FIGS. 4A-4B.

Figure 5A:
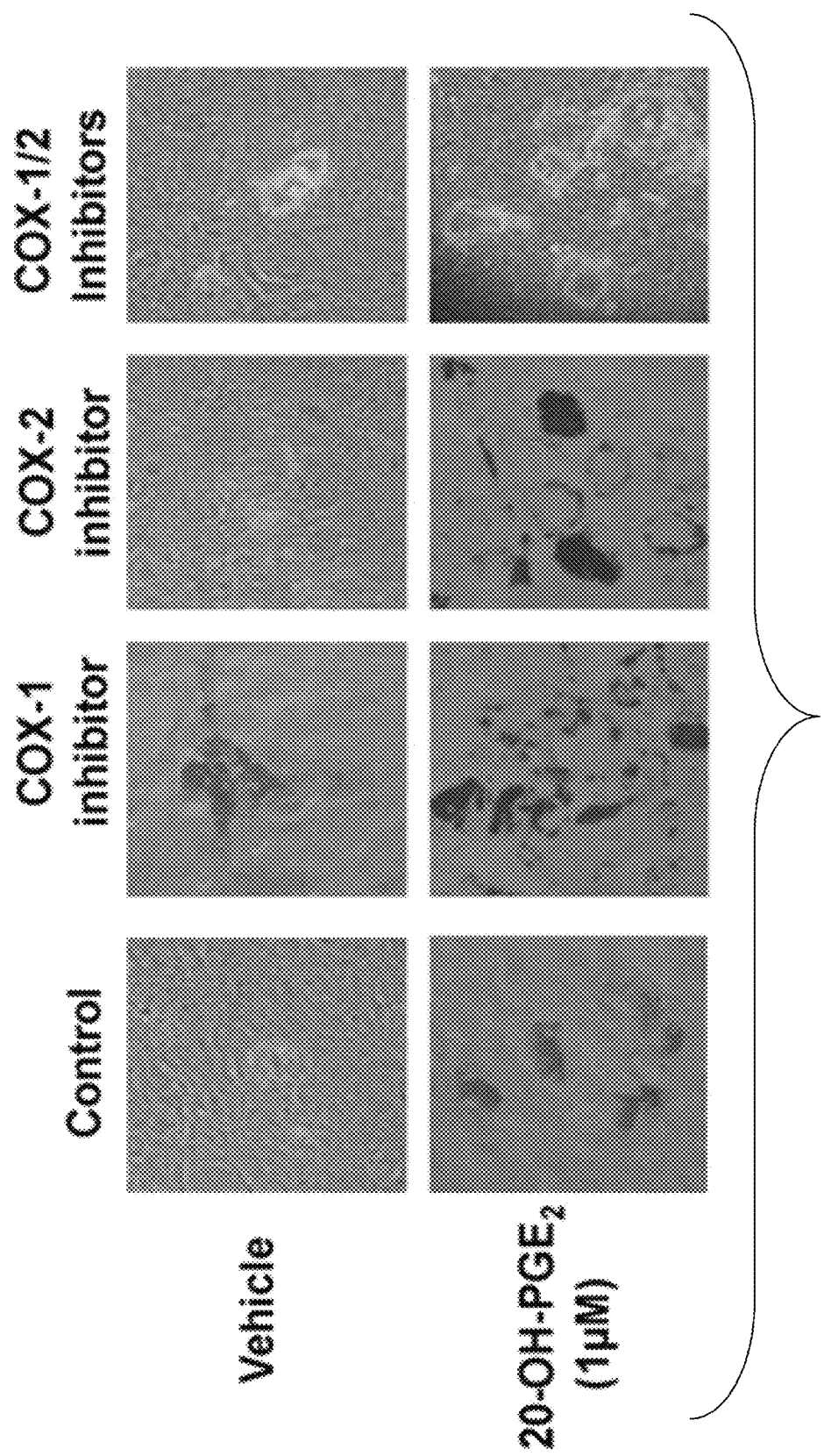
FIGS. 5A-5B: Effect of 20-OH-$PGE_2$ on adipogenesis in the presence and absence of COX-1 inhibitor and/or COX-2 inhibitor.
Figure 5B:
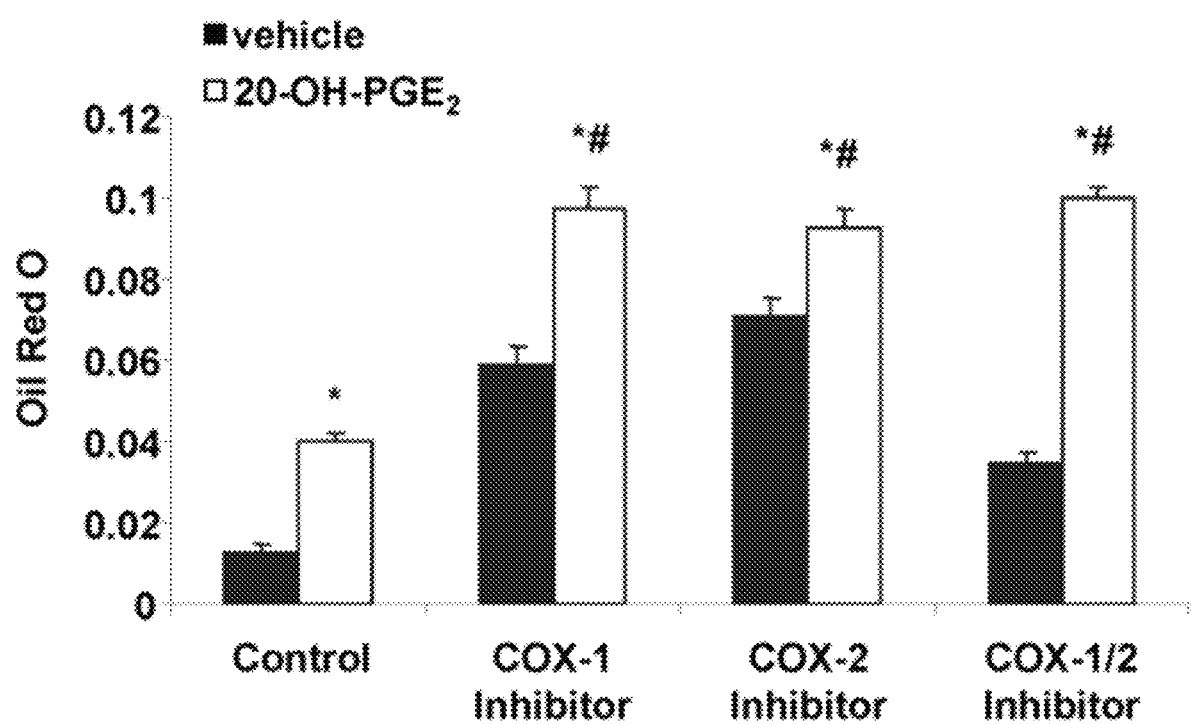
Figure 6A:
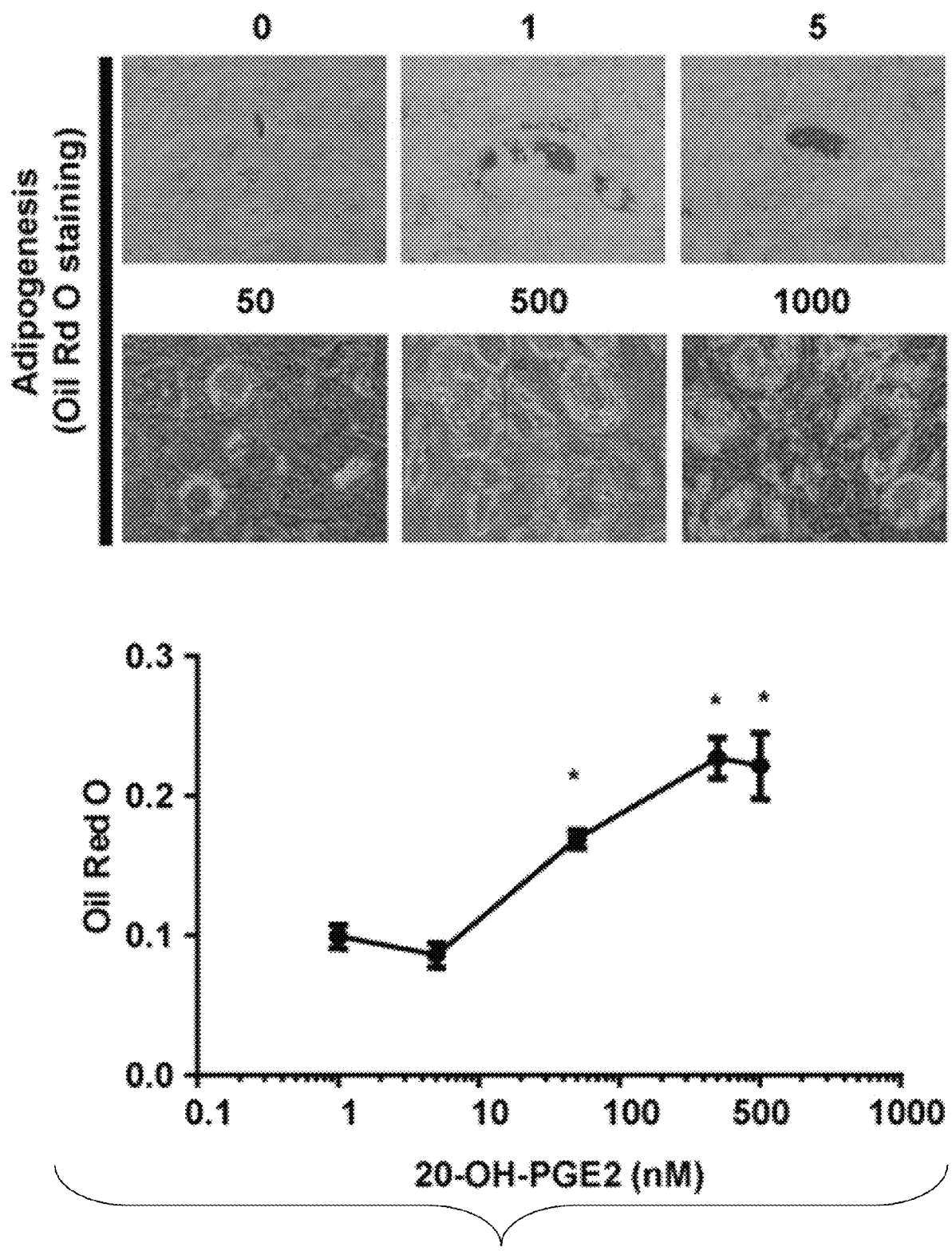
FIG. 6A: Concentration-dependent effect of 20-OH-$PGE_2$ on adipogenesis. Mean±SE, *P<0.05 versus 1 nM concentration of 20-OH-$PGE_2$. Mean±SE, *P<0.05, and **P<0.01 versus control.
Figure 6B:
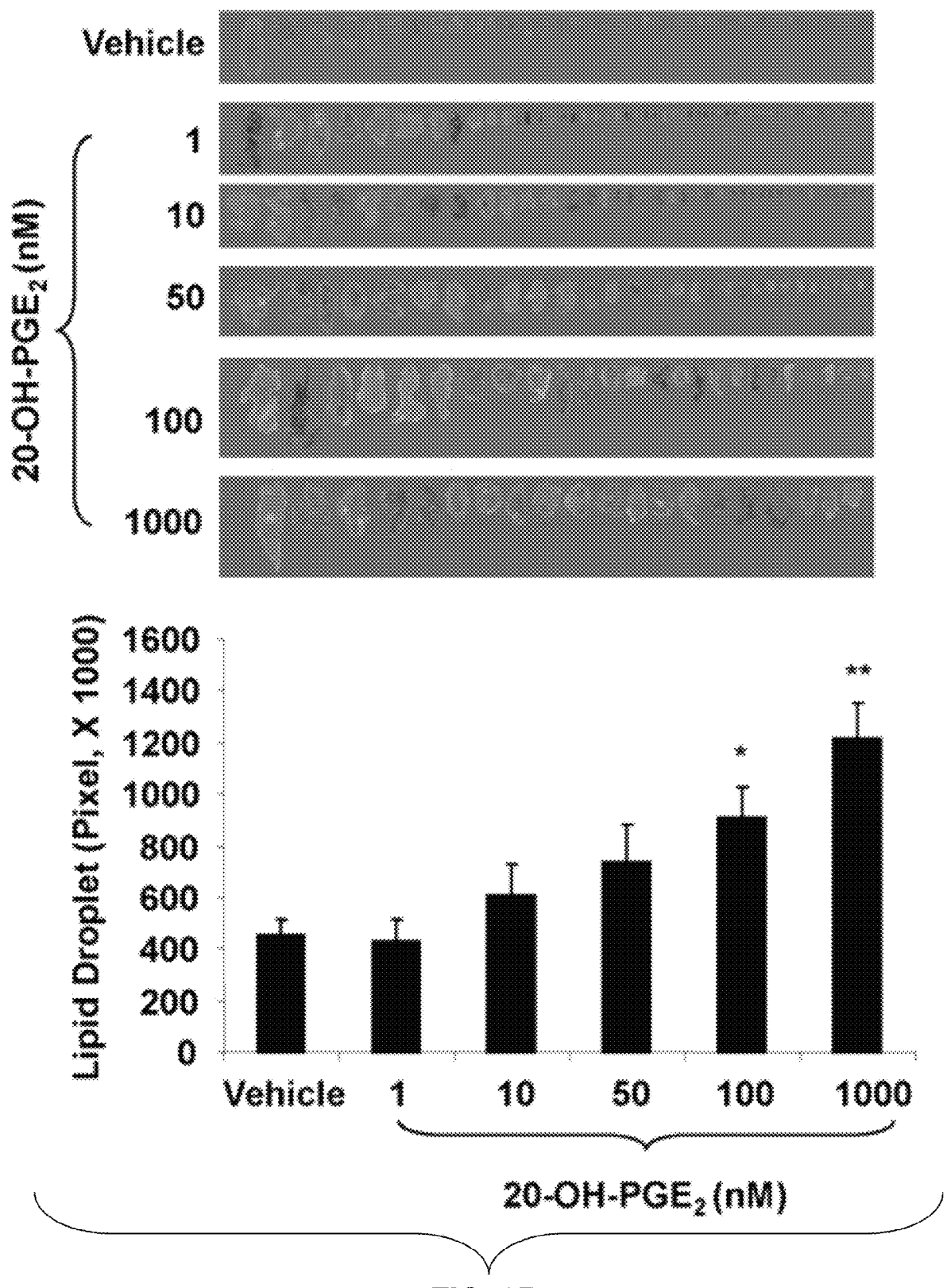
FIG. 6B: Effect of 20-OH-$PGE_2$ on adipocyte size. Mean±SE, *P<0.05, and **P<0.01 versus control.

The effects of 20-OH-PGE$_2$ on adipogensis in the presence or absence of COX-1 and COX-2 inhibitors were evaluated. 20-OH-PGE$_2$ stimulated (P>0.05) adipogenesis 4-fold as measured by lipid accumulation (FIGS. 5A-5B). Neither COX-1 inhibitor nor COX-2 inhibitor, alone or together, prevented 20-OH-PGE$_2$-mediated increase in adipogenesis, indicating a COX-independent action of this metabolite. As seen from FIG. 6A, the effect of 20-OH-PGE$_2$ was concentration dependent. 20-OH-PGE$_2$ significantly increased lipid accumulation at 50 nM and had maximal effect at 500 nM. In addition, 20-OH-PGE$_2$ stimulated adipocyte hypertrophy as measured by lipid droplet size. As seen in FIG. 6B, lipid droplet size increased 2- and 3-fold in response to concentrations of 100 nM and 1,000 nM, respectively, of 20-OH-PGE$_2$. These results indicate that the COX-2 metabolite 20-OH-PGE$_2$ plays a significant role in inducing adipogenesis and that its effect may be antagonized by PGE$_2$.

Figure 7A:
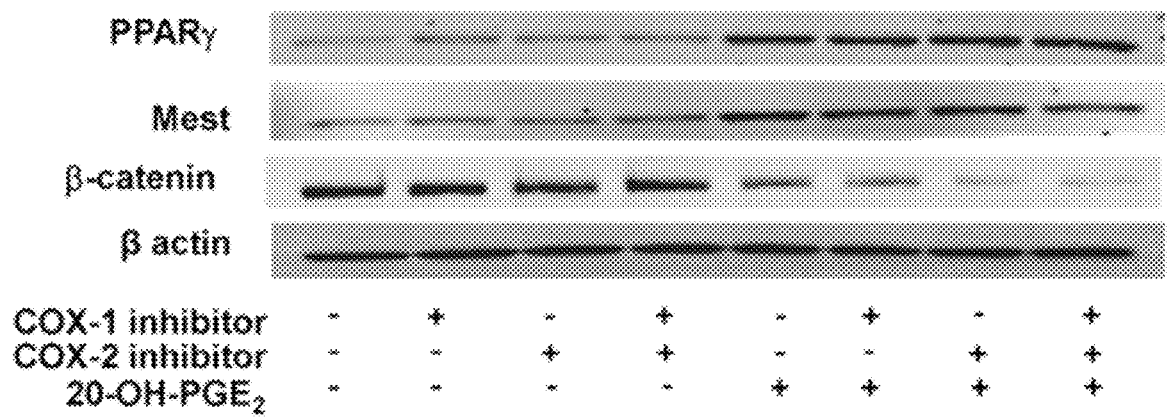
FIGS. 7A-7D: Effect of 20-OH-$PGE_2$ on adipogenic markers.
Figure 7B:
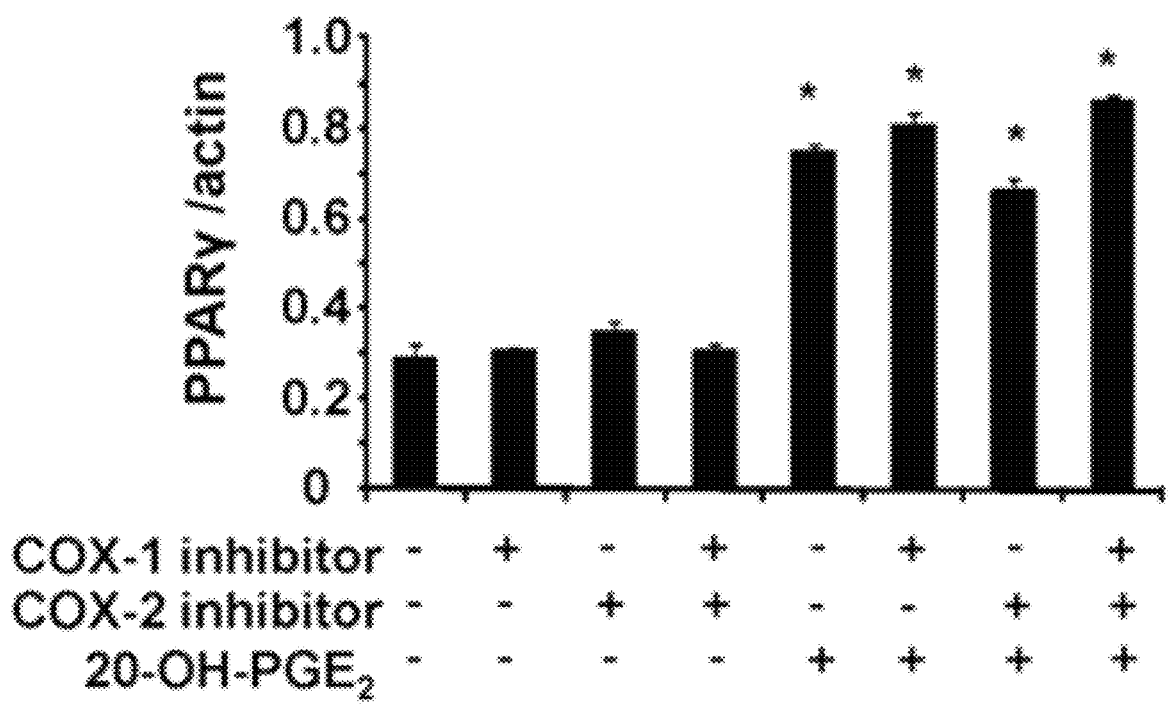
Figure 7C:
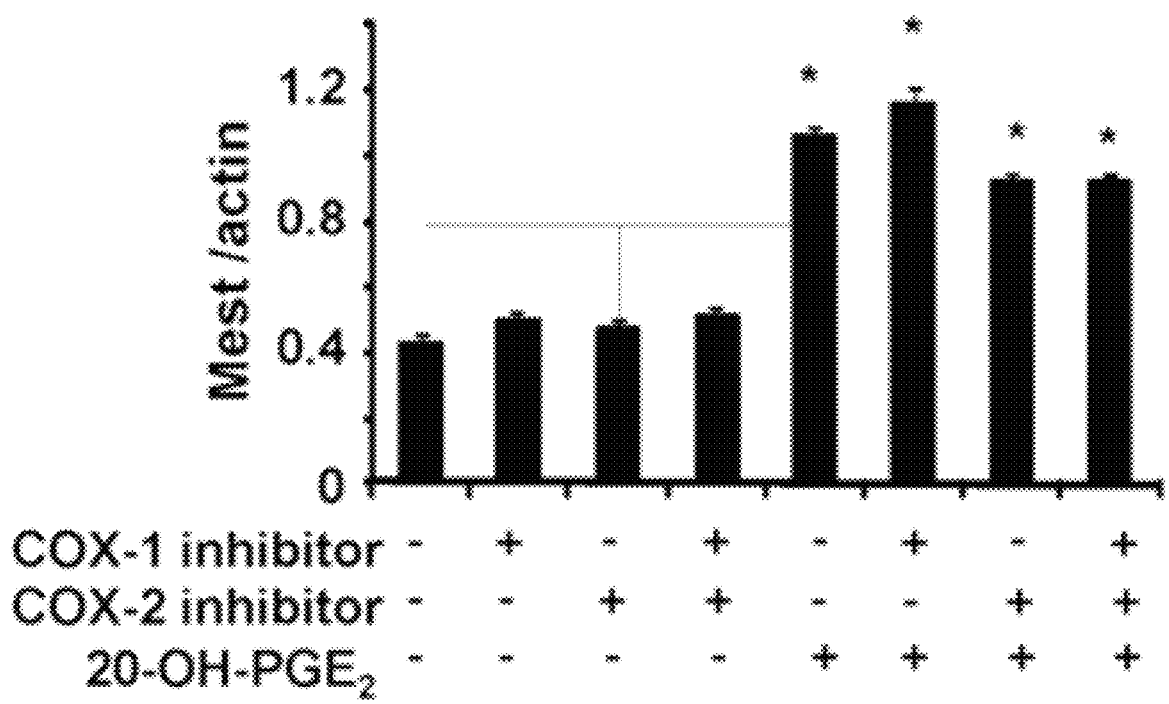
Figure 7D:
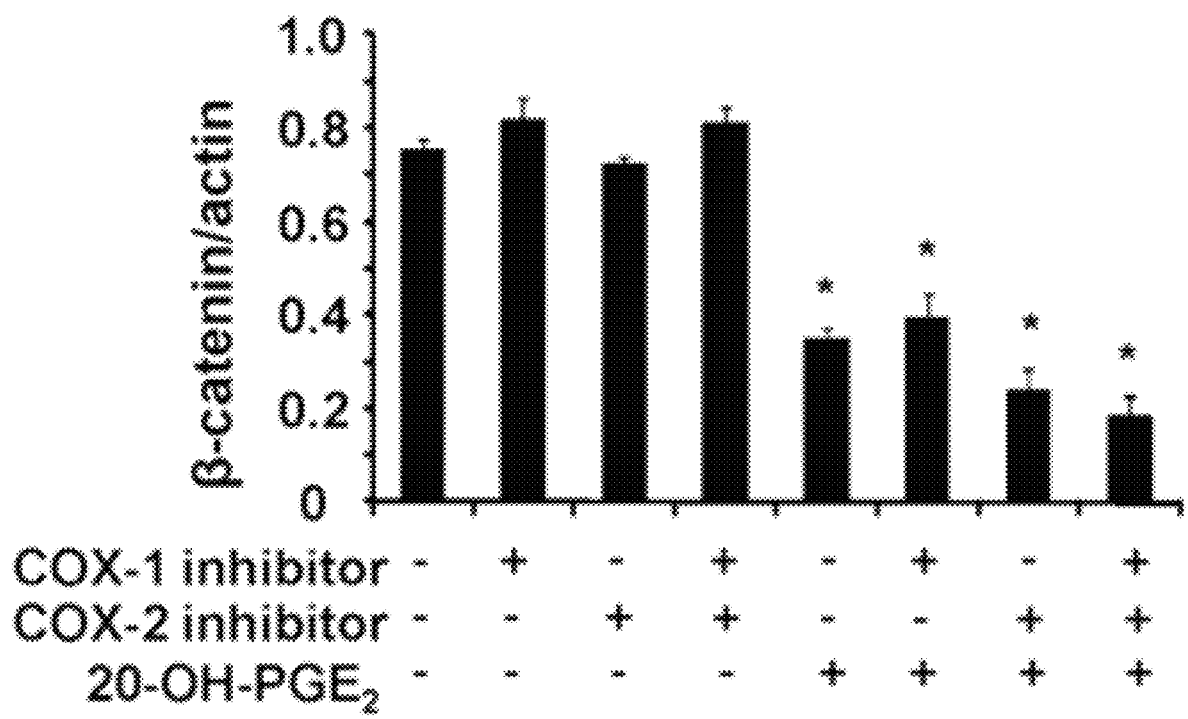

The effects of 20-OH-PGE$_2$ on β-catenin, PPARγ, and Mest expression as adipogenic differentiation markers, in the presence and absence of COX-1 and COX-2 inhibitors, were examined. (FIGS. 7A-7D.) Densitometry analysis showed that the expression of PPARγ and Mest (FIG. 7B and FIG. 7C, respectively) was significantly increased in the presence of 20-OH-PGE$_2$ when the cells were treated with COX-1 inhibitor, COX-2 inhibitor, or both. In contrast, as seen in FIG. 7D, β-catenin expression significantly decreased in the presence of 20-OH-PGE$_2$ when the cells were treated with COX-1 inhibitor, COX-2 inhibitor, or both. Similar data were obtained with 20-HETE, except that in the presence of a COX-2 inhibitor, the effect was blunted.

Figure 8:
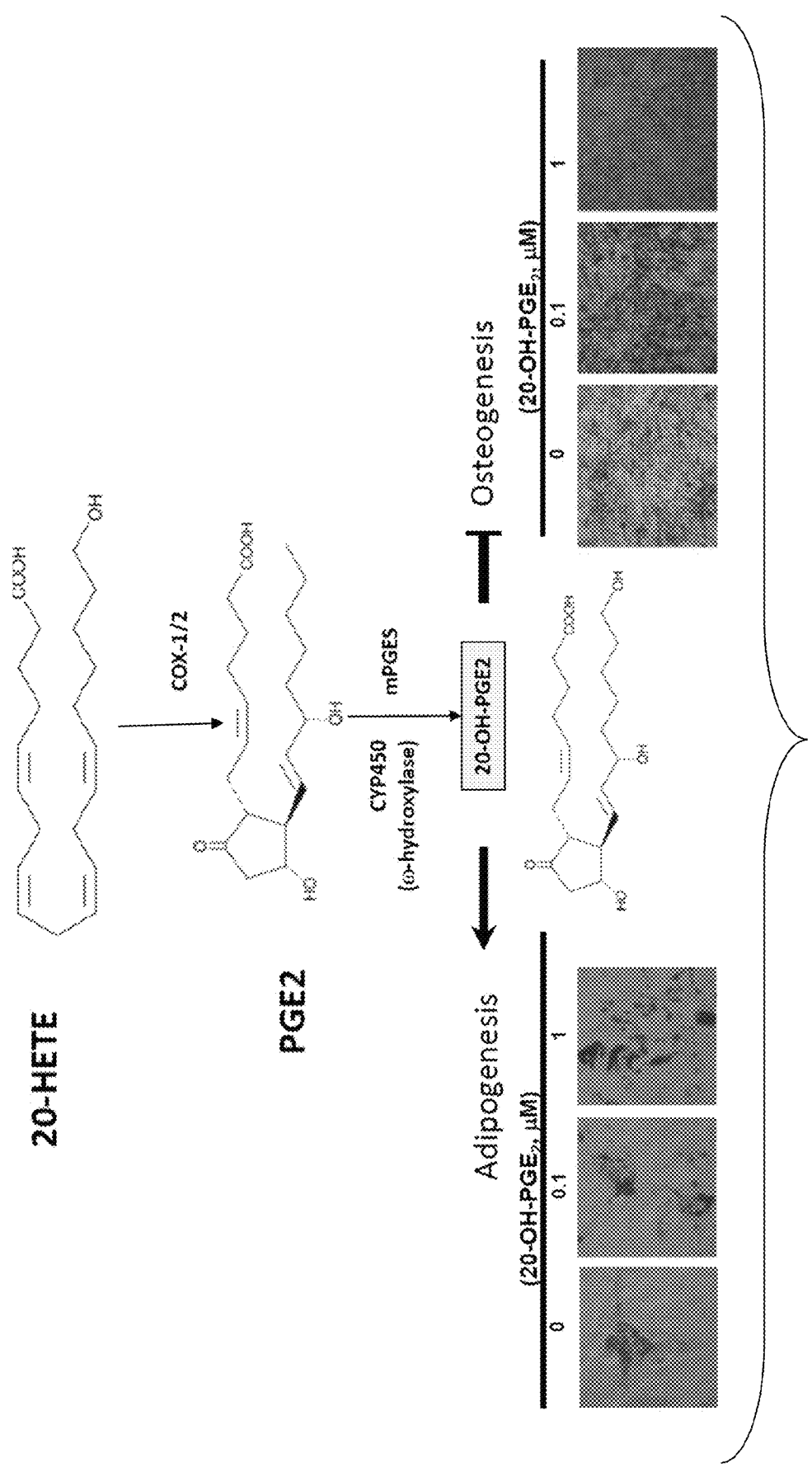
FIG. 8: Concentration-dependent effect of 20-OH-PGE$_2$ on adipogenesis and osteogenesis.

The effect of 20-OH-PGE$_2$ on mesenchymal stem cells was evaluated. As shown in FIGS. 8-11, 20-OH-PGE$_2$ blocked bone formation, meaning mesenchymal stem cells form fat over bone upon contact with 20-OH-PGE$_2$. FIG. 8 is a summary of the effects of 20-OH-PGE$_2$ with increasing concentration on both adipogenesis and osteogenesis. As seen from the stained mesenchymal cell pictures in this figure, fat formation increased with increasing 20-OH-PGE$_2$ concentration, and bone formation decreased with increasing 20-OH-PGE$_2$ concentration.

Figure 9:
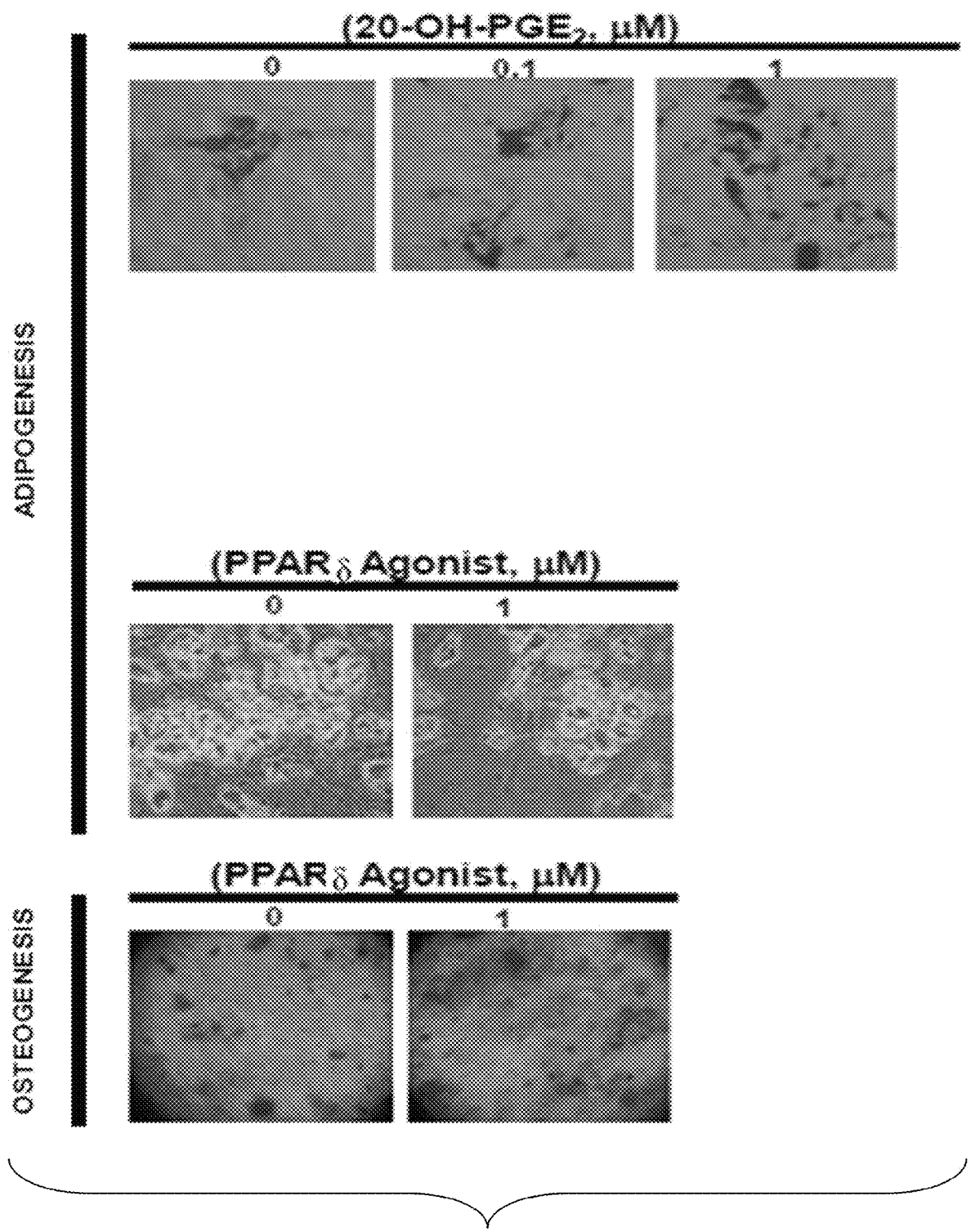
FIG. 9: Stained mesenchymal cells exposed to varying concentrations of 20-OH-PGE$_2$ and a PPARδ agonist.

FIG. 9 shows images of stained mesenchymal cells with varying concentrations of 20-OH-PGE$_2$ and a PPARδ agonist. The images reveal adipogenesis increased with increasing concentrations of 20-OH-PGE$_2$, but decreased with increasing concentrations of the PPARδ agonist. The images further reveal an increase in osteogenesis with increasing concentration of the PPARδ agonist.

Figure 10A:
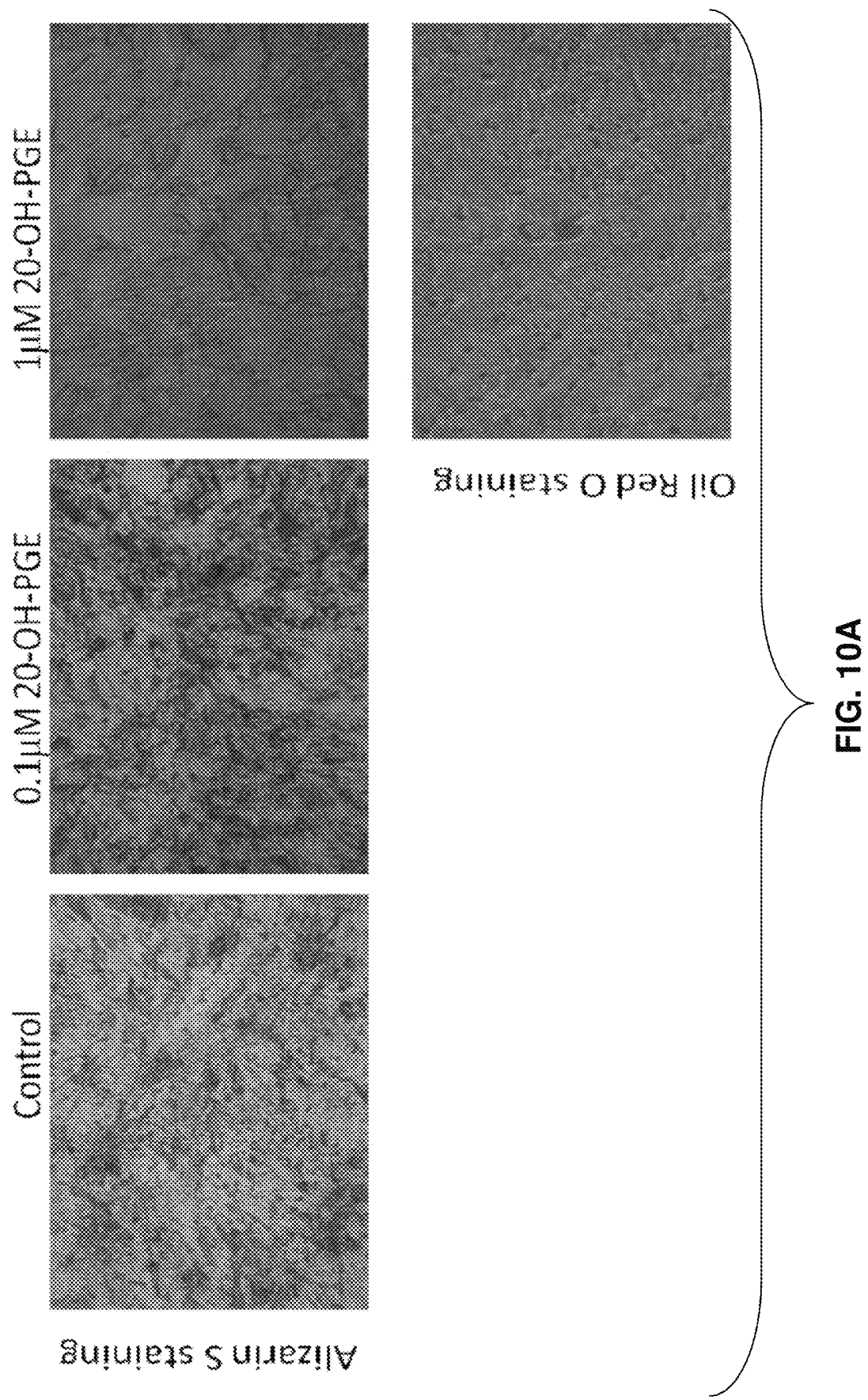
FIG. 10A: Osteogenesis effects of 20-OH-PGE$_2$ on mesenchymal cells stained with Alizarin S and Oil Red O.
Figure 10B:
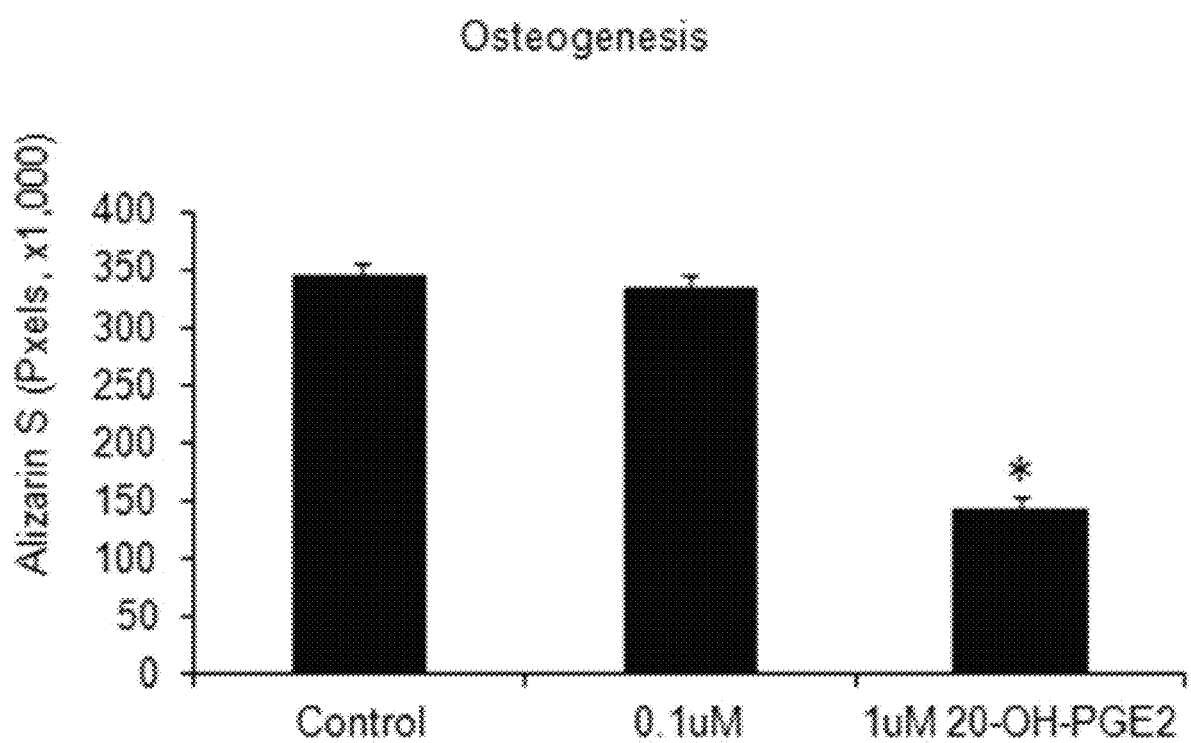
FIG. 10B: Effect of 20-OH-PGE$_2$ on osteogenesis from BM-derived mesenchymal stem cells. *Control versus 1 µM, P<0.01.

FIG. 10A depicts the osteogenesis effects of 20-OH-PGE$_2$ on mesenchymal cells stained with Alizarin S and Oil O. FIG. 10B shows the effects of 20-OH-PGE$_2$ on osteogenesis from BM-derived mesenchymal stem cells. As seen from the chart in this figure, osteogenesis decreased with increasing concentration of 20-OH-PGE$_2$. This also shows that osteogenesis decreased with increasing concentration of 20-OH-PGE$_2$.

Figure 11A:
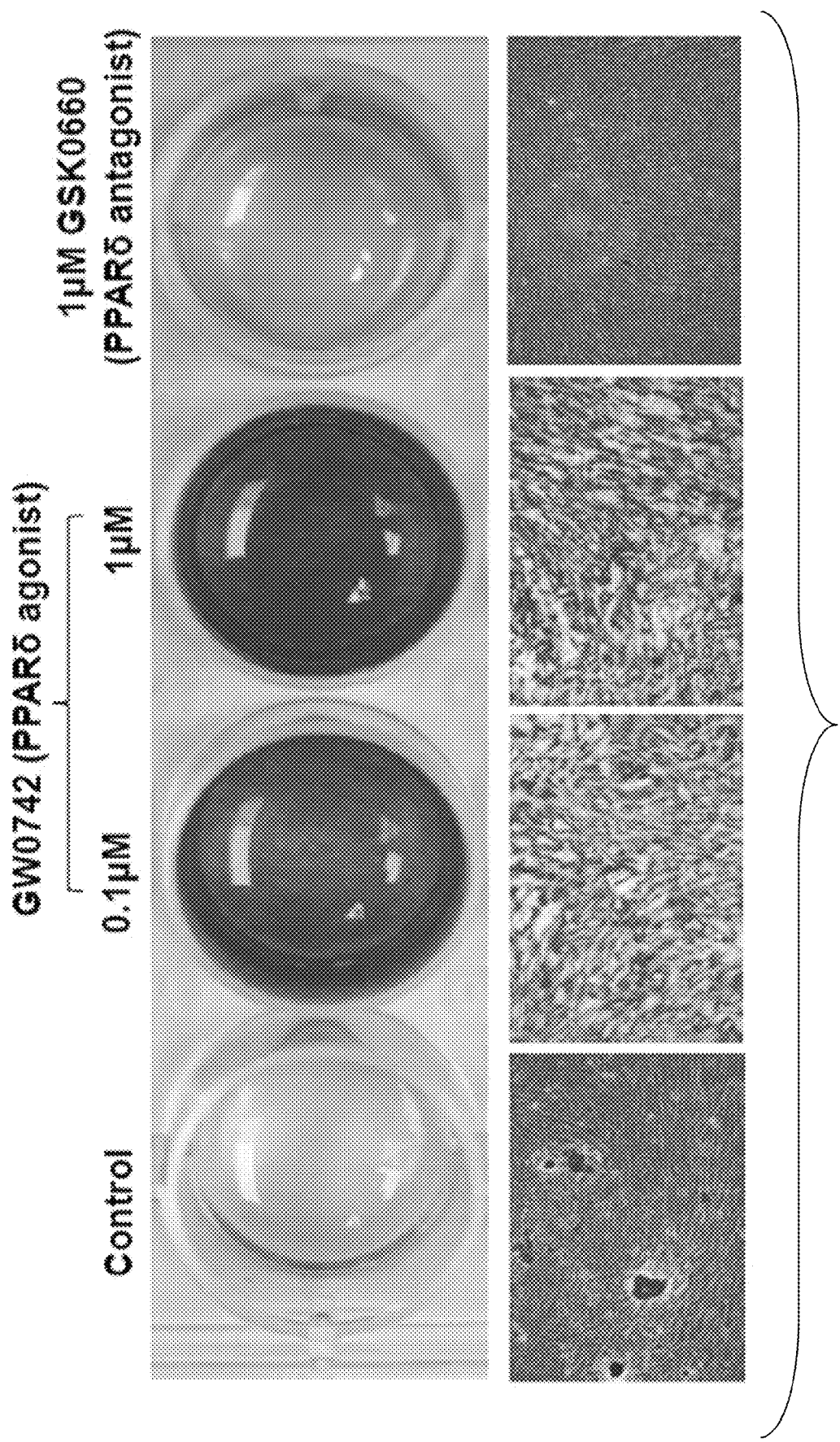
FIGS. 11A-11B: hBM-derived MSCs treated with the PPARδ agonist (GW0742) and PPARδ antagonist (GSK0660) every 2 days during osteogenesis. Increased red staining on GW0742 at 0.1 µM and 1 µM shows an increase in osteogenesis. Decreased red staining on GSK0660 at 1 µM shows a decrease in osteogenesis. *p<0.01, † p<0.001.
Figure 11B:
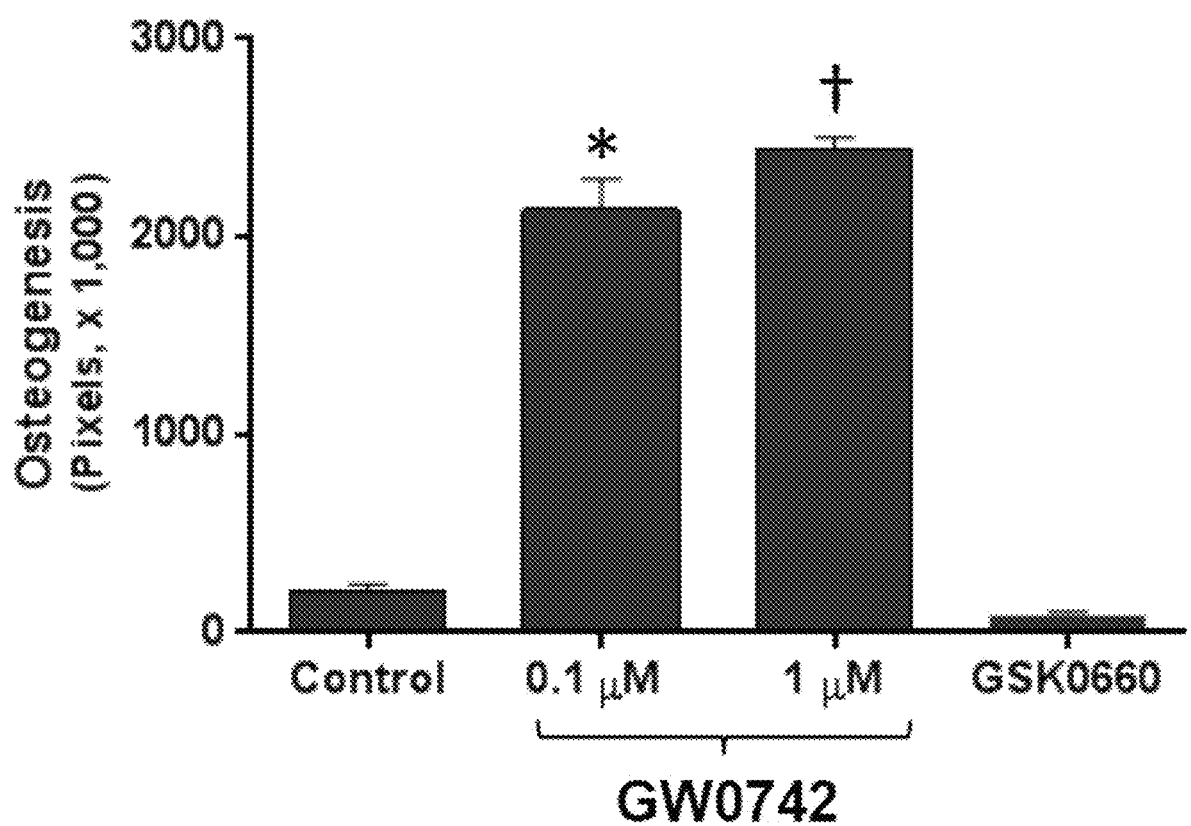

Example 2—Effects of GW0742 and GSK0660 hBM-derived MSCs were treated with GW0742 (a PPARδ agonist) and GSK0660 (a PPARδ antagonist) every 2 days during osteogenesis. Cells were stained with 2% Alizarin S, and images were taken from 24 well plates under a microscope. FIG. 11A shows four of these microscope images. Mineralization was quantified with Metamorph software. As seen in FIG. 11B, increased red staining on the PPARδ agonist (GW0742) was observed at 0.1 μM and 1 μM, indicating an increase in osteogenesis, and decreased red staining on the PPARδ antagonist (GSK0660) was observed at 1 μM, indicating a decrease in osteogenesis.

Example 3—Synthesis of Target Compound 6a

Compound 6a was prepared via Scheme 1, shown in FIG. 12.

Synthesis of 4-methyl-2-phenylthiazole-5-carboxylic Acid Ethyl Ester (1a)

To a suspension of thiobenzamide (6.05 g, 0.044 mol) in 95% ethanol was added ethyl 2-chloroacetoacetate (6.10 mL, 0.044 mol), and the mixture was stirred at reflux temperature for 26 hours. The reaction mixture was concentrated under reduced pressure and the resulting residue was suspended in ice-cold hexane and stirred for 20 minutes. The suspension was filtered and collected as a cream-colored solid (7.434 g, 0.030 mol, 68.3%). TLC R$_f$ (25% EtOAc/Hexane)=0.63. Mp 84-87° C. $^1$H NMR (CDCl$_3$, 600 MHz): δ ppm 8.19 (2H, d, J=7.32 Hz), 7.56 (1H, t, J=7.32), 7.53 (2H, t, J=7.08), 4.41 (2H, q, J=7.14), 2.94 (3H, s), 1.41 (3H, t, J=7.14). $^{13}$C NMR (CDCl$_3$, 150 MHz): δ (ppm) 171.25, 161.07, 157.83, 133.21, 129.82, 128.10, 122.55, 62.37, 16.29, 14.52 ppm.

Synthesis of 4-methyl-2-phenyl-5-thiazolemethanol (2a)

To a stirred solution of ethyl ester 1a (0.303 g, 1.237 mmol) in anhydrous THF (1 mL) at 0° C. was added 2M lithium aluminum hydride solution in THF (1.24 ml, 2.48 mmol). The resulting mixture was stirred under argon at 0° C. for 1.5 hours. The reaction mixture was quenched by the careful addition of 0.5 ml of water, followed by 2.5 ml of ethyl acetate and 0.92 g of anhydrous sodium sulfate. The mixture was stirred for 15 minutes and was filtered and concentrated under reduced pressure to give 2a as a light-yellow solid (0.215 g, 1.053 mmol, 85.1%). TLC R$_f$ (25% EtOAc/Hexane)=0.11. Mp 101-102° C. $^1$H NMR (CDCl$_3$, 600 MHz): δ ppm 7.88 (2H, d, J=7.92 Hz), 7.41 (3H, m), 4.79 (2H, s), 2.94 (1H, s), 2.41 (3H, s).

Synthesis of 4-hydroxycinnamic Acid Methyl Ester (3)

To a stirred solution of p-coumaric acid (0.704 g, 4.288 mmol) in anhydrous methanol (10 ml) was added concentrated H$_2$SO$_4$ (1 ml) and was heated at reflux temperature for 20 hours. The mixture was cooled to room temperature and concentrated under reduced pressure. The residue was dissolved in ethyl acetate, washed with water, dried with Na$_2$SO$_4$, and concentrated. The residue was purified by column chromatography on silica gel to give 3 as a white solid (0.574 g, 3.221 mmol, 75.1%). TLC R$_f$ (25% EtOAc/Hexane)=0.18. Mp 137-138° C. $^1$H NMR (CDCl$_3$, 600 MHz): δ ppm 7.65 (1H, d, J=16.02 Hz), 7.44 (2H, d, J=8.58), 6.86 (2H, d, J=8.58), 6.31 (1H, d, J=15.98), 5.57 (1H, s), 3.81 (3H, s).

Synthesis of 5-(chloromethyl)-4-methyl-2-phenyl-thiazole (4a)

To a stirred solution of alcohol 2a (4.095 g, 0.019 mol) in anhydrous dichloromethane (100 ml) was added triethylamine (5.50 ml, 0.039 mol). The resulting mixture was cooled to 4° C. and methanesulfonyl chloride (2.30 ml, 0.029 mol) was slowly added. The mixture was stirred at 4° C. for 24 hours and then diluted with 100 ml dichloromethane, washed with saturated NaHCO$_3$ solution, water, brine, dried with Na$_2$SO$_4$, and concentrated. The residue was purified by column chromatography on silica gel with 10% ethyl acetate/hexane to give 4a as a light yellow solid (2.850 g, 0.013 mol, 64.0%). TLC R$_f$ (25% EtOAc/Hexane)=0.57. Mp 89-90° C. $^1$H NMR (CDCl$_3$, 600 MHz): δ ppm 7.90 (2H, m), 7.43 (3H, m), 4.80 (2H, s), 2.50 (3H, s).

Synthesis of [4-[[4-methyl-2-phenylthiazol-5-yl]methyl]methoxy]cinnamic Acid Methyl Ester (5a)

To a stirred solution of methyl ester 3 (0.142 g, 0.797 mmol) and chloromethyl 4a (0.150 g, 0.670 mmol) in anhydrous acetonitrile (5 ml) was added cesium carbonate with partial solubility. The resulting mixture was stirred for 24 hours at room temperature at which TLC showed that the chloromethyl 4a had been consumed. The reaction mixture was concentrated and the residue was dissolved in ethyl acetate and washed with water, brine, dried with Na$_2$SO$_4$, and concentrated. Column chromatography on silica gel failed to give a pure product and the crude white solid 5 collected was moved to the next step without further purification.

Synthesis of [4-[[4-methyl-2-phenylthiazol-5-yl]methyl]methoxy]cinnamic Acid (6a)

To a stirred solution of methyl ester 5 was added dropwise 3M NaOH. After 20 hours, the mixture was acidified with 1M HCl to a pH=1-2 and concentrated. The residue was suspended in ethyl acetate and washed with water and brine. The aqueous phase was extracted with a separate portion of ethyl acetate and the organic phases were combined, dried with Na$_2$SO$_4$, and concentrated. The residue was purified by column chromatography on silica gel to give 6a as a white solid (0.061 g, 0.173 mmol, 41.7%). TLC R$_f$ (50% EtOAc/Hexane)=0.17. Mp 209-211° C. $^1$H NMR (Acetone-d6, 600 MHz): δ ppm 7.91 (2H, m), 7.67 (2H, d, J=8.76), 7.55 (1H, d, 15.96), 7.49 (3H, m), 7.09 (2H, d, J=8.82), 6.41 (1H, d, J=15.96), 5.38 (2H, s), 2.46 (4H, s).

Example 4—Synthesis of Target Compound 6*b*

Compound 6b was prepared via Scheme 1, shown in FIG. 12.

Synthesis of 4-methyl-2-[4-(trifluoromethyl)phenyl]-thiazole-5-carboxylic Acid Ethyl Ester (1b)

In analogy to the procedure described above to produce 1a, 4-(trifluoromethyl)thiobenzamide (1.065 g, 5.190 mmol) was treated with ethyl-2-chloroacetoacetate in 95% ethanol to give 1b as a cream-colored solid (1.148 g, 3.644 mmol, 70.2%). TLC R$_f$ (25% EtOAc/Hexane)=0.69. Mp 89-89.5° C.

Synthesis of 4-methyl-2-[4-(trifluoromethyl)phenyl]-thiazole-5-methanol (2b)

In analogy to the procedure described above to produce 2a, ethyl ester 1b (1.320 g, 4.190 mmol) was treated with 2M LiAlH$_4$ solution in THF to give 2b as a yellow solid (0.904 g, 3.308 mmol, 79.0%). TLC R$_f$ (25% EtOAc/Hexane) =0.16. Mp 121.5-122° C.

Synthesis of 5-(chloromethyl)-4-methyl-2-[4-(trifluoromethyl)phenyl]-thiazole (4b)

In analogy to the procedure described above to produce 4a, alcohol 2b (0.883 g, 3.231 mmol) was treated with methanesulfonyl chloride and triethylamine in dry DCM to give 4b as a light yellow solid (0.790 g, 2.708 mmol, 83.8%). TLC R$_f$ (25% EtOAc/Hexane)=0.53. Mp 68.5-69° C.

Synthesis of [4-[[4-methyl-2-[4-(trifluoromethyl)phenyl]-thiazol-5-yl]methyl]methoxy]cinnamic Acid Methyl Ester (5b)

In analogy to the procedure described above to produce 5a, chloromethyl 4b (0.331 g, 1.135 mmol) and methyl ester 3 were treated with cesium carbonate in anhydrous acetonitrile to give 5b as a light yellow solid (0.365 g, 0.842 mmol, 74.3%). TLC R$_f$ (25% EtOAc/Hexane)=0.32. Mp 153-155° C.

Synthesis of [4-[[4-methyl-2-[4-(trifluoromethyl)phenyl]-thiazol-5-yl]methyl]methoxy]cinnamic acid (6b)

In analogy to the procedure described above to produce 6a, methyl ester 5b (0.202 g, 0.466 mmol) was treated with 3M NaOH in 95% ethanol to give 6b as a white solid (0.048 g, 0.114 mmol, 24.6%). TLC R$_f$ (50% EtOAc/Hexane)=0.15. Mp 224-225° C. $^1$H NMR (Acetone-d6, 600 MHz): δ ppm 8.18 (2H, d, J=8.10), 7.84 (2H, d, J=8.22), 7.68 (2H, d, J=8.76), 7.64 (1H, d, J=16.02), 7.13 (2H, d, J=8.82), 6.42 (1H, d, J=15.96), 5.44 (2H, s), 2.52 (3H, s).

Example 5—Synthesis of Target Compound 6c

Compound 6c was prepared via Scheme 1, shown in FIG. 12.

Synthesis of 4-methyl-2-[3-(trifluoromethyl)phenyl]-thiazole-5-carboxylic Acid Ethyl Ester (1c)

In analogy to the procedure described above to produce 1a, 3-(trifluoromethyl)thiobenzamide (0.501 g, 2.442 mmol) was treated with ethyl-2-chloroacetoacetate in 95% ethanol to give 1c as a cream-colored solid (0.567 g, 1.790 mmol, 73.7%). TLC R$_f$ (25% EtOAc/Hexane)=0.63. Mp 90-91° C.

Synthesis of 4-methyl-2-[3-(trifluoromethyl)phenyl]-thiazole-5-methanol (2c)

In analogy to the procedure described above to produce 2a, ethyl ester 1c (2.053 g, 6.516 mmol) was treated with 2M LiAlH$_4$ solution in THF to give 2c as a yellow oil (1.273 g, 4.658 mmol, 71.5%). TLC R$_f$ (25% EtOAc/Hexane)=0.16.

Synthesis of 5-(chloromethyl)-4-methyl-2-[3-(trifluoromethyl)phenyl]-thiazole (4c)

In analogy to the procedure described above to produce 4a, alcohol 2c (1.295 g, 4.739 mmol) was treated with methanesulfonyl chloride and triethylamine in dry DCM to give 4c as a light yellow solid (0.830 g, 2.846 mmol, 60.1%). TLC R$_f$ (25% EtOAc/Hexane)=0.61. Mp 42-43° C.

Synthesis of [4-[[4-methyl-2-[3-(trifluoromethyl)phenyl]-thiazol-5-yl]methyl]methoxy]cinnamic Acid Methyl Ester (5c)

In analogy to the procedure described above to produce 5a, chloromethyl 4c (0.472 g, 1.618 mmol) and methyl ester 3 were treated with cesium carbonate in anhydrous acetonitrile to give 5c as a yellow-white solid (0.551 g, 1.270 mmol, 80.5%). TLC $R_f$ (25% EtOAc/Hexane)=0.30. Mp 125-127° C.

Synthesis of [4-[[4-methyl-2-[3-(trifluoromethyl) phenyl]-thiazol-5-yl]methyl]methoxy]cinnamic Acid (6c)

In analogy to the procedure described above to produce 6a, methyl ester 5c (0.207 g, 0.477 mmol) was treated with 3M NaOH in 95% ethanol to give 6c as a white solid (0.138 g, 0.329 mmol, 69.0%). TLC $R_f$ (50% EtOAc/Hexane)= 0.40. Mp 179.5-181° C. $^1$H NMR (Acetone-d6, 600 MHz): δ ppm 8.29 (1H, s), 8.23 (1H, d, J=7.8), 7.84 (1H, d, J=7.8), 7.76 (1H, t, J=7.8), 7.69 (2H, d, J=8.7), 7.67 (1H, d, J=16.02), 7.15 (2H, d, J=8.76), 6.44 (1H, d, J=15.96), 5.46 (2H, s), 2.54 (3H, s).

Example 6—Effects of Compounds 6a-6c on Adipogenesis and Osteogenesis

Figure 16:
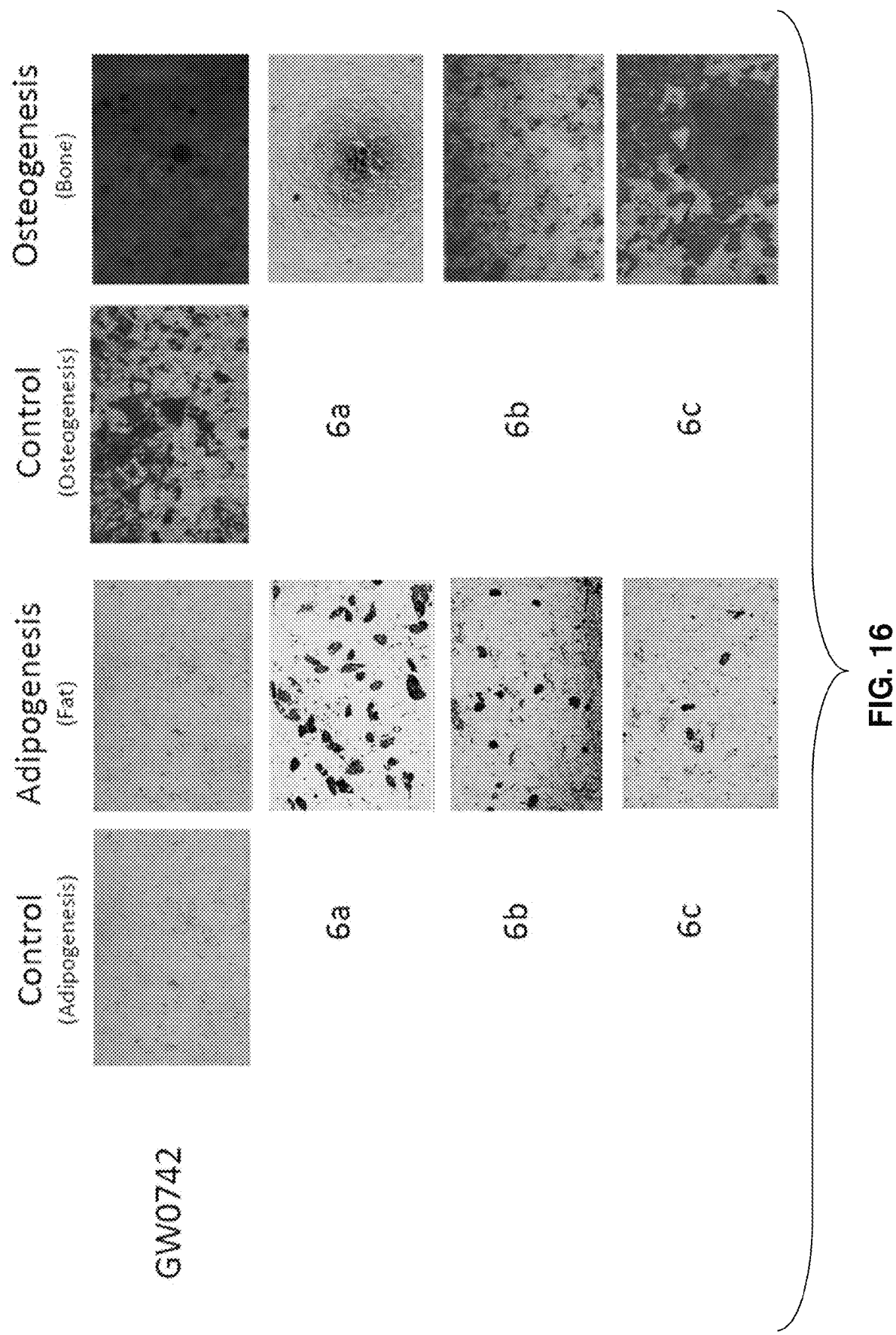
FIG. 16: Effects of GW0742, compound 6a, compound 6b, and compound 6c on adipogenesis and osteogenesis.

The effects of compounds 6a, 6b, and 6c on adipogenesis and osteogenesis were evaluated. MSCs were treated with compounds 6a, 6b, and 6c as described above for GW0742. FIG. 15 shows a table summarizing the results of these assays. As seen in FIG. 15, compound 6a increased adipogenesis versus osteogenesis, and compound 6c increased osteogenesis versus adipogenesis. These results are also shown in FIG. 16, alongside the effects of GW0742 described above.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed:

1. A compound comprising a structural formula of Formula I which comprises JF-4-80:

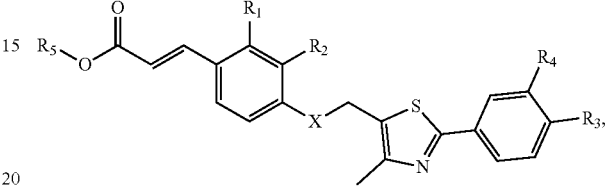

wherein:
X is S;
$R_1$ is H;
$R_2$ is H;
$R_3$ is $CF_3$;
$R_4$ is F; and
$R_5$ is H;
and salts, isomers, stereoisomers, enantiomers, racemates, solvates, hydrates, polymorphs, and prodrugs thereof.

2. A pharmaceutical composition comprising:
a compound of any of claim 1, and
a pharmaceutically acceptable carrier, excipient, diluent, or adjuvant.

3. The pharmaceutical composition of claim 2, wherein the compound is present at a concentration ranging from about 0.1 μM to about 1 μM.

* * * * *